(12) United States Patent
Bunker et al.

(10) Patent No.: US 10,653,681 B2
(45) Date of Patent: May 19, 2020

(54) ANALGESIC COMPOUNDS

(71) Applicant: Recurium IP Holdings, LLC, San Diego, CA (US)

(72) Inventors: Kevin Duane Bunker, Escondido, CA (US); Deborah Helen Slee, Encinitas, CA (US); Chad Daniel Hopkins, San diego, CA (US); Joseph Robert Pinchman, San Diego, CA (US); Mehmet Kahraman, San Diego, CA (US); Peter Qinhua Huang, San Diego, CA (US)

(73) Assignee: Recurium IP Holdings, LLC, San Diego, CA (US)

( * ) Notice: Subject to any disclaimer, the term of this patent is extended or adjusted under 35 U.S.C. 154(b) by 0 days.

(21) Appl. No.: 16/085,505

(22) PCT Filed: Mar. 15, 2017

(86) PCT No.: PCT/US2017/022430
§ 371 (c)(1),
(2) Date: Sep. 14, 2018

(87) PCT Pub. No.: WO2017/160922
PCT Pub. Date: Sep. 21, 2017

(65) Prior Publication Data
US 2019/0111031 A1    Apr. 18, 2019

Related U.S. Application Data

(60) Provisional application No. 62/309,338, filed on Mar. 16, 2016.

(51) Int. Cl.

| | | |
|---|---|---|
| *A61K 31/433* | (2006.01) | |
| *A61K 31/137* | (2006.01) | |
| *A61K 31/167* | (2006.01) | |
| *A61K 31/415* | (2006.01) | |
| *A61K 31/421* | (2006.01) | |
| *A61K 31/4245* | (2006.01) | |
| *A61K 31/426* | (2006.01) | |
| *A61K 31/44* | (2006.01) | |
| *A61K 31/505* | (2006.01) | |
| *C07D 213/38* | (2006.01) | |
| *C07D 271/113* | (2006.01) | |
| *C07D 233/12* | (2006.01) | |
| *C07D 285/08* | (2006.01) | |
| *C07D 277/42* | (2006.01) | |
| *C07D 239/42* | (2006.01) | |
| *C07C 233/07* | (2006.01) | |
| *C07D 263/48* | (2006.01) | |
| *C07C 233/15* | (2006.01) | |
| *C07D 231/12* | (2006.01) | |
| *A61K 31/165* | (2006.01) | |

(Continued)

(52) U.S. Cl.
CPC .......... *A61K 31/433* (2013.01); *A61K 31/136* (2013.01); *A61K 31/137* (2013.01); *A61K 31/165* (2013.01); *A61K 31/167* (2013.01); *A61K 31/415* (2013.01); *A61K 31/421* (2013.01); *A61K 31/426* (2013.01); *A61K 31/4245* (2013.01); *A61K 31/44* (2013.01); *A61K 31/505* (2013.01); *A61P 29/00* (2018.01); *C07C 211/29* (2013.01); *C07C 211/52* (2013.01); *C07C 233/07* (2013.01); *C07C 233/13* (2013.01); *C07C 233/15* (2013.01); *C07C 233/25* (2013.01); *C07D 213/38* (2013.01); *C07D 213/73* (2013.01); *C07D 231/12* (2013.01); *C07D 233/12* (2013.01); *C07D 239/42* (2013.01); *C07D 263/48* (2013.01); *C07D 271/113* (2013.01); *C07D 277/28* (2013.01); *C07D 277/32* (2013.01); *C07D 277/40* (2013.01); *C07D 277/42* (2013.01); *C07D 285/08* (2013.01); *C07D 285/12* (2013.01); *C07D 285/125* (2013.01); *C07D 285/135* (2013.01); *A61K 9/0019* (2013.01); *A61K 9/0053* (2013.01); *A61K 45/06* (2013.01)

(58) Field of Classification Search
CPC .. A61K 31/136; A61K 31/137; A61K 31/165; A61K 31/167; A61K 31/415; A61K 31/421; A61K 31/4245; A61K 31/426; A61K 31/433; A61K 31/44; A61K 31/505; A61K 45/06; A61K 9/0019; A61K 9/005; A61P 29/00; C07C 211/29; C07C 211/52; C07C 233/07; C07C 233/13; C07C 233/15; C07C 233/25; C07D 213/38; C07D 213/73; C07D 231/12; C07D 233/12; C07D 239/42; C07D 263/48; C07D 271/113; C07D 277/28; C07D 277/32; C07D 277/40; C07D 277/42; C07D 285/08; C07D 285/12; C07D 285/125; C07D 285/135
See application file for complete search history.

(56) References Cited

U.S. PATENT DOCUMENTS 2,883,391 A    4/1959 Swain
4,508,911 A    4/1985 Kaplan
(Continued)

FOREIGN PATENT DOCUMENTS

BE    893479    10/1982
DE    10261091    7/2004
(Continued)

OTHER PUBLICATIONS

Alegaon, S.G. et al., "Novel imidazo[2,1-b][1,3,4]thiadiazole carrying rhodanine-3-acetic acid as potential antitubercular agents" *Bioorganic & Medicinal Chemistry Letters* (2012) 22:1917-1921.

(Continued)

*Primary Examiner* — Savitha M Rao
(74) *Attorney, Agent, or Firm* — Knobbe, Martens, Olson & Bear, LLP

(57) ABSTRACT

Disclosed herein are compounds of Formula (I), methods of synthesizing compounds of Formula (I), and methods of using compounds of Formula (I) as an analgesic.

12 Claims, No Drawings

(51) Int. Cl.
| | |
|---|---|
| C07D 277/32 | (2006.01) |
| C07D 285/12 | (2006.01) |
| C07D 277/28 | (2006.01) |
| C07C 211/29 | (2006.01) |
| C07C 233/13 | (2006.01) |
| C07D 277/40 | (2006.01) |
| C07D 213/73 | (2006.01) |
| C07D 285/125 | (2006.01) |
| C07C 233/25 | (2006.01) |
| C07C 211/52 | (2006.01) |
| C07D 285/135 | (2006.01) |
| A61P 29/00 | (2006.01) |
| A61K 31/136 | (2006.01) |
| A61K 9/00 | (2006.01) |
| A61K 45/06 | (2006.01) |

(56) References Cited

U.S. PATENT DOCUMENTS

| | | | |
|---|---|---|---|
| 4,593,025 | A | 6/1986 | Sempuku et al. |
| 5,594,022 | A | 1/1997 | Norwell et al. |
| 5,610,184 | A | 3/1997 | Shahinian, Jr. |
| 5,854,234 | A | 12/1998 | Hansen et al. |
| 6,638,933 | B2 | 10/2003 | Gerlach et al. |
| 2004/0204398 | A1 | 10/2004 | Bakshi et al. |
| 2004/0209959 | A1 | 10/2004 | Hogestatt et al. |
| 2005/0288308 | A1 | 12/2005 | Amrien et al. |
| 2006/0002545 | A1 | 1/2006 | George et al. |
| 2006/0222690 | A1 | 10/2006 | Bley |
| 2006/0223837 | A1 | 10/2006 | Codd et al. |
| 2007/0155738 | A1 | 7/2007 | Steeneck et al. |
| 2008/0021026 | A1 | 1/2008 | Kahraman et al. |
| 2008/0081822 | A1 | 4/2008 | Berry et al. |
| 2009/0076106 | A1 | 3/2009 | Sorensen et al. |
| 2010/0240671 | A1 | 9/2010 | Zhuo |
| 2011/0159005 | A1 | 6/2011 | Jacobson et al. |
| 2011/0288120 | A1* | 11/2011 | Khanzhin ............ C07D 217/26 514/309 |
| 2012/0108583 | A1 | 5/2012 | Gharat et al. |
| 2013/0196952 | A1 | 8/2013 | Bunnage et al. |
| 2013/0303525 | A1 | 11/2013 | Sasmal et al. |
| 2014/0134261 | A1 | 5/2014 | Singh et al. |
| 2015/0283117 | A1 | 10/2015 | Gharat et al. |
| 2016/0031873 | A1 | 2/2016 | Yao et al. |

FOREIGN PATENT DOCUMENTS

| | | |
|---|---|---|
| EP | 0402752 | 12/1990 |
| WO | WO 2000/021943 | 4/2000 |
| WO | WO 2003/093250 | 11/2003 |
| WO | WO 2004/000294 | 12/2003 |
| WO | WO 2004/054582 | 7/2004 |
| WO | WO 2004/063161 | 7/2004 |
| WO | WO 2004/072066 | 8/2004 |
| WO | WO 2005/009941 | 2/2005 |
| WO | WO 2007/140439 | 12/2007 |
| WO | WO 2008/002959 | 1/2008 |
| WO | WO 2008/010921 | 1/2008 |
| WO | WO 2008/100622 | 8/2008 |
| WO | WO 2008/111604 | 9/2008 |
| WO | WO 2009/068512 | 6/2009 |
| WO | WO 2009/139834 | 11/2009 |
| WO | WO 2010/056758 | 5/2010 |
| WO | WO 2013/059648 | 4/2013 |
| WO | WO 2014/129431 | 8/2014 |
| WO | WO 2014/167444 | 10/2014 |
| WO | WO 2015/184003 | 12/2015 |

OTHER PUBLICATIONS

Bramley, S.E. et al., "The Hantzsch Thiazole Synthesis under Acidic Conditions: Change of Regioselectivity" *Journal of the Chemistry Society, Perkin Transactions* 1 (1987) 639-643.

Cameron, M. et al., "The Expedient Synthesis of 4,2'-Difluoro-5'-(7-trifluoromethyl-imidazo[1,2 a]pyrimidin-3-yl)biphenyl-2-carbonitrile, a GABA a2/3 Agonist" *Organic Process Research & Development* (2006) 10:398-402.

Cocco, M.T. et al., "Synthesis of ibuprofen heterocyclic amides and investigation of their analgesic and toxicological properties" *European Journal of Medicinal Chemistry* (2003) 38:513-518.

Decker, M. D. et al., "The therapeutic potential of nicotinic acetylcholine receptor agonists for pain control" *Expert Opinion on Investigational Drugs* (2001) 10(10), 1819-1830.

Fresno, N. et al., "Adamantyl Analogues of Paracetamol as Potent Analgesic Drugs via Inhibition of TRPA1", *PLOS One* (Dec. 1, 2014) 9(12) e113841:1-16.

Freynhagen, R. et al., "Efficacy of pregabalin in neuropathic pain evaluated in a 12-week, randomised, double-blind, multicentre, placebo-controlled trial of flexible- and fixed-dose regimens" *Pain* (2005) 115:254-263.

Froyen, P., "Phosphorus in Organic Synthesis. Acyloxyphosphonium Salts as Chemoselective Acylating Reagents" *Tetrahedron Letters* (1997) 38:5359-5362.

Hilfiker, M.A. et al., "Discovery of novel aminothiadiazole amides as selective EP3 receptor antagonists" *Bioorganic & Medicinal Chemistry Letters* (2009) 19:4292-4295.

Li, G.B. et al., "Drug Discovery against Psoriasis: Identification of a New Potent FMSlike Tyrosine Kinase 3 (FLT3) Inhibitor, 1-(4-((1H-Pyrazolo[3,4-d]pyrimidin-4-yl)oxy)-3-fluorophenyl)-3-(5-(tertbutyl) isoxazol-3-yl)urea, That Showed Potent Activity in a Psoriatic Animal Model" *Journal of Medicinal Chemistry* (2016) 59:8293-8305.

Lohitha, P. et al., "Synthesis and Pharmacological evaluation of Schiff's and Mannich bases of Indole Derivatives" *RGUHS Journal of Pharmaceutical Sciences* (2011) 1(1):69-78.

Kino, T. et al., "Trifluoromethylation of various aromatic compounds by CF3I in the presence of Fe(II) compound, H2O2 and dimethylsulfoxide" *Journal of Fluorine Chemistry* (2010) 131:98-105.

Kurouchi, H. et al., "Protonation Switching to the Least-Basic Heteroatom of Carbamate through Cationic Hydrogen Bonding Promotes the Formation of Isocyanate Cations" *Chemistry—A European Journal* (2014) 20:8682-8690.

Madhavi, K. et al. "Synthesis of Cyanoacetylated Derivatives of Some Heteroaryl Amines as Analgesic and Antioxidant Agents" *International Journal of Pharmaceutical Sciences and Nanotechnology* (2013) 5(4):1879-1884.

Max, M. B. M.D. et al., "Effects of Desipramine, Amitriptyline, and Fluoxentine of Pain in Diabetic Neuropathy" *New England Journal of Medicine* (1992) 326:1250-1256.

Melnikova, I., "Pain market" *Nat. Rev Drug Discovery* (2010) 9(8):589-590.

Niu, P. et al., "Synthesis of 2-Amino-1,3,4-oxadiazoles and 2-Amino-1,3,4- thiadiazoles via Sequential Condensation and 12-Mediated Oxidative C—O/C—S Bond Formation" *The Journal of Organic Chemistry* (2015) 80:1018-1024.

Raju, D. N. et al. "Synthesis, Characterization and Analgesic Activity of Some Novel Substituted 2-Amino Benzothiazole Derivatives" *World Journal of Pharmacy and Pharmaceutical Sciences* (2015) 4(5):1815-1821.

Reuter, R. et al., "Synthesis and Property Studies of Cyclotrisazobenzenes" *European Journal of Organic Chemistry* (2009) 5647-5652.

Sinning, C. et al. "New Analgesics Synthetically Derived from the Paracetamol Metabolite N-(4 Hydroxyphenyl)-(5Z,8Z,11Z,14Z)-icosatetra-5,8,11,14-enamide" *J. Med. Chem.* (2008) 51(24):7800 7805.

Sippy, K. B. et al., "Preparation and characterization of N-(3-pyridinyl) spirocyclic diamines as ligands for nicotinic acetylcholine receptors" *Bioorganic and Medicinal Chemistry Letters* (2009) 19:1682-1685.

Wolf, V. et al., "Über 2-Amino-oxazole und ihre 2-[p-Aminobenzolsulfonyl]-Derivate" *Chemische Berichte* (1962) 95:2419-2423.

(56) References Cited

OTHER PUBLICATIONS

Xiang, J. et al., "Synthesis and biological evaluation of sulfonamidooxazoles and b-keto sulfones: selective inhibitors of 11b-hydroxysteroid dehydrogenase type I" *Bioorganic & Medicinal Chemistry Letters* 15 (2005) 2865-2869.

Zhang, C. X. et al., "Synthesis and analgesic activity of secondary amine analogues of pyridylmethylamine and positional isomeric analogues of ABT-594" *Bioorganic and Medicinal Chemistry Letters* (2006) 16:2013-2016.

Notification of Transmittal of the International Search Report and the Written Opinion of the International Searching Authority, or the Declaration dated Jun. 23, 2017 for PCT/US2017/022430, filed Mar. 15, 2017.

Written Opinion of the International Searching Authority dated Jun. 23, 2017 for PCT Application No. PCT/US2017/022430, filed Mar. 15, 2017.

\* cited by examiner

ANALGESIC COMPOUNDS

BACKGROUND

Field

The present application relates to the fields of chemistry, biochemistry and medicine. More particularly, disclosed herein are aromatic and heteroaromatic compounds. Also disclosed herein are methods of using aromatic and heteroaromatic compounds as an analgesic.

Description

Nonsteroidal anti-inflammatory compounds, or NSAIDs, are an extremely useful group of small molecule drugs, typified by acetylsalicylic acid, ibuprofen and naproxen. These are often sold without prescription, and are variously used to treat pain, inflammation, and fever. However, NSAIDs can have undesirable side effects, including gastric upset and/or gastric bleeding.

Acetaminophen, also known as paracetamol or APAP, is also an effective pain reliever often sold over the counter (without prescription). Although it shares analgesic and antipyretic properties with NSAIDs, it has only weak anti-inflammatory properties, and is thus not an NSAID. Unlike many NSAIDs, acetaminophen does not cause gastric upset or bleeding in prescribed doses. Thus, it is an extremely useful drug for those wishing analgesia without adverse gastric side effects.

Acetaminophen has the structure:

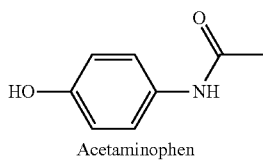

Acetaminophen

Acetaminophen is often combined with other drugs for relief of symptoms of influenza and the common cold, among other indications. It is particularly useful in combination with opioid analgesics, where it exhibits synergistic analgesic properties and allows patients to achieve adequate pain relief with lower doses of opioids. The most widely prescribed drug in the United States is a combination of acetaminophen and hydrocodone, with over 130 million prescriptions in the year 2010. Other acetaminophen-opioid combinations, including combinations with oxycodone, are also widely prescribed.

Acetaminophen poisoning is the most common cause of acute liver failure in the Western world, and acetaminophen accounts for the most drug overdoses in the English-speaking world. Acetaminophen is metabolized to form N-acetyl-p-benzoquinoneimine (NAPQI), which depletes glutathione in the liver, and if the glutathione is sufficiently depleted, as is the case with an acetaminophen overdose, the NAPQI metabolite injures hepatocytes leading to acute liver failure and often death. The acetaminophen-opioid combination drugs are commonly implicated in such toxicity, for various reasons. First, patients might not recognize that the prescribed pain relievers contain acetaminophen, and may supplement with acetaminophen if pain relief is inadequate. Second, continued administration of opioids can lead to tolerance and the need for increased dosages to obtain a comparable opioid analgesic effect, and users or abusers of the combination drugs may exceed safe dosages of acetaminophen as a consequence.

This has led the U.S. FDA to seek reduced amounts of acetaminophen in the opioid combination drugs and has also led an FDA advisory panel to recommend banning such drugs all together. Although the acetaminophen-opioid drugs remain on the market, there is a strong need for a less toxic replacement without the same hepatotoxicity risks.

SUMMARY

Some embodiments described herein relate to a compound of Formula (I), or a pharmaceutically acceptable salt thereof.

Some embodiments described herein related to a pharmaceutical composition that can include an effective amount of a compound of Formula (I), or a pharmaceutically acceptable salt thereof.

Some embodiments described herein related to using a compound of Formula (I), or a pharmaceutically acceptable salt thereof, in the preparation of a medicament for reducing or at least partially preventing pain and/or fever. Other embodiments described herein related to a method for reducing or at least partially preventing pain and/or fever that can include administering an effective amount of a compound of Formula (I), or a pharmaceutically acceptable salt thereof, to a subject in need thereof. Still other embodiments described herein related to a method for reducing or at least partially preventing pain and/or fever that can include contacting a cell in the central and/or peripheral nervous system of a subject with an effective amount of a compound of Formula (I), or a pharmaceutically acceptable salt thereof, to a subject in need thereof. Yet still other embodiments described herein related to the use of a compound of Formula (I), or a pharmaceutically acceptable salt thereof, for reducing or at least partially preventing pain and/or fever.

DETAILED DESCRIPTION

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) individually and independently selected from deuterium (D), halogen, hydroxy, $C_{1-4}$ alkoxy, $C_{1-8}$ alkyl, $C_{3-20}$ cycloalkyl, aryl, heteroaryl, heterocyclyl, $C_{1-8}$ haloalkyl, cyano, $C_{2-8}$ alkenyl, $C_{2-8}$ alkynyl, $C_{3-20}$ cycloalkenyl, aryl(alkyl), heteroaryl(alkyl), heterocyclyl(alkyl), acyl, thiocarbonyl, O-carbamyl, N-carbamyl, O-thiocarbamyl, N-thiocarbamyl, C-amido, N-amido, C-thioamido, N-thioamido, S-sulfonamido, N-sulfonamido, C-carboxy, O-carboxy, sulfenyl, sulfinyl, sulfonyl, haloalkoxy, an amino, a mono-substituted amino group and a di-substituted amino group.

As used herein, "$C_a$ to $C_b$" in which "a" and "b" are integers refer to the number of carbon atoms in a group. The indicated group can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated, the broadest range described in these definitions is to be assumed.

If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together," it means that they are covalently bonded, either indirectly through intermediate atoms, or directly to one another, to form a ring, for example:

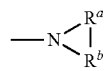

As used herein, the term "alkyl" refers to a fully saturated aliphatic hydrocarbon group. The alkyl moiety may be branched or straight chain. Examples of branched alkyl groups include, but are not limited to, iso-propyl, sec-butyl, t-butyl and the like. Examples of straight chain alkyl groups include, but are not limited to, methyl, ethyl, n-propyl, n-butyl, n-pentyl, n-hexyl, n-heptyl and the like. The alkyl group may have 1 to 30 carbon atoms (whenever it appears herein, a numerical range such as "1 to 30" refers to each integer in the given range; e.g., "1 to 30 carbon atoms" means that the alkyl group may consist of 1 carbon atom, 2 carbon atoms, 3 carbon atoms, etc., up to and including 30 carbon atoms, although the present definition also covers the occurrence of the term "alkyl" where no numerical range is designated). The alkyl group may also be a medium size alkyl having 1 to 12 carbon atoms. The alkyl group could also be a lower alkyl having 1 to 6 carbon atoms. An alkyl group may be substituted or unsubstituted.

The term "alkenyl" used herein refers to a monovalent straight or branched chain radical of from two to thirty carbon atoms containing a carbon double bond(s) including, but not limited to, 1-propenyl, 2-propenyl, 2-methyl-1-propenyl, 1-butenyl, 2-butenyl and the like. An alkenyl group may be unsubstituted or substituted.

The term "alkynyl" used herein refers to a monovalent straight or branched chain radical of from two to thirty carbon atoms containing a carbon triple bond(s) including, but not limited to, 1-propynyl, 1-butynyl, 2-butynyl and the like. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused, bridged or spiro fashion. As used herein, the term "fused" refers to two rings which have two atoms and one bond in common. As used herein, the term "bridged cycloalkyl" refers to compounds wherein the cycloalkyl contains a linkage of one or more atoms connecting non-adjacent atoms. As used herein, the term "spiro" refers to two rings which have one atom in common and the two rings are not linked by a bridge. Cycloalkyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A cycloalkyl group may be unsubstituted or substituted. Typical mono-cycloalkyl groups include, but are in no way limited to, cyclopropyl, cyclobutyl, cyclopentyl, cyclohexyl, cycloheptyl and cyclooctyl. Examples of fused cycloalkyl groups are decahydronaphthalenyl, dodecahydro-1H-phenalenyl and tetradecahydroanthracenyl; examples of bridged cycloalkyl groups are bicyclo[1.1.1]pentyl, adamantanyl, and norbornanyl; and examples of spiro cycloalkyl groups include spiro[3.3]heptane and spiro[4.5]decane.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). Cycloalkenyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). When composed of two or more rings, the rings may be connected together in a fused, bridged or spiro fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. Cycloalkynyl groups can contain 8 to 30 atoms in the ring(s), 8 to 20 atoms in the ring(s) or 8 to 10 atoms in the ring(s). When composed of two or more rings, the rings may be joined together in a fused, bridged or spiro fashion. A cycloalkynyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms (for example, 1, 2 or 3 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused or spiro fashion. Additionally, any nitrogens in a heteroalicyclic may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and/or 3,4-methylenedioxyphenyl).

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroalkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl and imidazolylalkyl and their benzo-fused analogs.

A "heteroalicyclyl(alkyl)" and "heterocyclyl(alkyl)" refer to a heterocyclic or a heteroalicyclylic group connected, as a substituent, via a lower alkylene group. The lower alkylene and heterocyclyl of a (heteroalicyclyl)alkyl may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl (methyl) and 1,3-thiazinan-4-yl(methyl).

"Lower alkylene groups" are straight-chained —CH$_2$— tethering groups, forming bonds to connect molecular fragments via their terminal carbon atoms. Examples include but are not limited to methylene (—CH$_2$—), ethylene (—CH$_2$CH$_2$—), propylene (—CH$_2$CH$_2$CH$_2$—) and butylene (—CH$_2$CH$_2$CH$_2$CH$_2$—). A lower alkylene group can be substituted by replacing one or more hydrogen of the lower alkylene group and/or by substituting both hydrogens on the same carbon with a cycloalkyl group

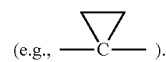

As used herein, the term "hydroxy" refers to a —OH group.

As used herein, "alkoxy" refers to the formula —OR wherein R is an alkyl, an alkenyl, an alkynyl, a cycloalkyl, a cycloalkenyl, aryl, heteroaryl, heterocyclyl, cycloalkyl (alkyl), aryl(alkyl), heteroaryl(alkyl) or heterocyclyl(alkyl) is defined herein. A non-limiting list of alkoxys is methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen, alkyl, alkenyl, alkynyl, aryl, heteroaryl, heterocyclyl, aryl(alkyl), heteroaryl(alkyl) and heterocyclyl(alkyl) connected, as substituents, via a carbonyl group. Examples include formyl, acetyl, propanoyl, benzoyl and acryl. An acyl may be substituted or unsubstituted.

A "cyano" group refers to a "—CN" group.

The term "halogen atom" or "halogen" as used herein, means any one of the radio-stable atoms of column 7 of the Periodic Table of the Elements, such as, fluorine, chlorine, bromine and iodine.

A "thiocarbonyl" group refers to a "—C(=S)R" group in which R can be the same as defined with respect to O-carboxy. A thiocarbonyl may be substituted or unsubstituted.

An "O-carbamyl" group refers to a "—OC(=O)N (R$_A$R$_B$)" group in which R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-carbamyl may be substituted or unsubstituted.

An "N-carbamyl" group refers to an "ROC(=O)N (R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-carbamyl may be substituted or unsubstituted.

An "O-thiocarbamyl" group refers to a "—OC(=S)—N (R$_A$R$_B$)" group in which R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-thiocarbamyl may be substituted or unsubstituted.

An "N-thiocarbamyl" group refers to an "ROC(=S)N (R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-thiocarbamyl may be substituted or unsubstituted.

A "C-amido" group refers to a "—C(=O)N(R$_A$R$_B$)" group in which R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A C-amido may be substituted or unsubstituted.

An "N-amido" group refers to a "RC(=O)N(R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-amido may be substituted or unsubstituted.

A "C-thioamido" group refers to a "—C(=S)N($R_A R_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A C-thioamido may be substituted or unsubstituted.

An "N-thioamido" group refers to a "RC(=S)N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-thioamido may be substituted or unsubstituted.

An "S-sulfonamido" group refers to a "—$SO_2$N($R_A R_B$)" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An S-sulfonamido may be substituted or unsubstituted.

An "N-sulfonamido" group refers to a "R$SO_2$N($R_A$)—" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-sulfonamido may be substituted or unsubstituted.

An "O-carboxy" group refers to a "RC(=O)O—" group in which R can be hydrogen, an alkyl, an alkenyl, an alkynyl, an alkoxy, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "sulfenyl" group refers to an "—SR" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "$SO_2$R" group in which R can be the same as defined with respect to sulfenyl. A sulfonyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

The term "amino" as used herein refers to a —$NH_2$ group.

A "mono-substituted amino" group refers to a "—NHR" group in which R can be an alkyl, an alkenyl, an alkynyl, a haloalkyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. A mono-substituted amino may be substituted or unsubstituted.

Examples of mono-substituted amino groups include, but are not limited to, —NH(methyl), —NH(phenyl) and the like.

A "di-substituted amino" group refers to a "—N$R_A R_B$" group in which $R_A$ and $R_B$ can be independently an alkyl, an alkenyl, an alkynyl, a haloalkyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. A di-substituted amino may be substituted or unsubstituted. Examples of di-substituted amino groups include, but are not limited to, —N(methyl)$_2$, —N(phenyl)(methyl), —N(ethyl)(methyl) and the like.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, a radical indicates species with a single, unpaired electron such that the species containing the radical can be covalently bonded to another species. Hence, in this context, a radical is not necessarily a free radical. Rather, a radical indicates a specific portion of a larger molecule. The term "radical" can be used interchangeably with the term "group."

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), a sulfuric acid, a nitric acid and a phosphoric acid (such as 2,3-dihydroxypropyl dihydrogen phosphate). Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, trifluoroacetic, benzoic, salicylic, 2-oxopentanedioic, or naphthalenesulfonic acid. Pharmaceutical salts can also be obtained by reacting a compound with a base to form a salt such as an ammonium salt, an alkali metal salt, such as a sodium, a potassium or a lithium salt, an alkaline earth metal salt, such as a calcium or a magnesium salt, a salt of a carbonate, a salt of a bicarbonate, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine. For compounds of Formula (I), those skilled in the art understand that when a salt is formed by protonation of a nitrogen-based group (for example, $NH_2$), the nitrogen-based group can be associated with a positive charge (for example, $NH_2$ can become $NH_3^+$) and the positive charge can be balanced by a negatively charged counterion (such as $Cl^-$).

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z, or a mixture thereof.

In some embodiments, in any compound described, all tautomeric forms are also intended to be included. For example, without limitation, a reference to the compound

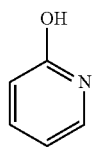

may be interpreted to include tautomer

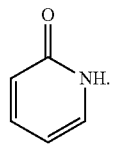

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

Compounds

Some embodiments disclosed herein generally relate to a compound of Formula (I), or a pharmaceutically acceptable salt thereof:

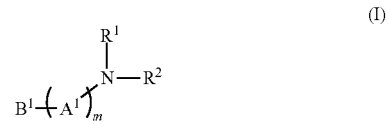

wherein: $B^1$ can be an optionally substituted phenyl, an optionally substituted 5-membered monocyclic heteroaryl or an optionally substituted 6-membered monocyclic heteroaryl; $R^1$ can be selected from H (hydrogen), D (deuterium), an optionally substituted $C_{1-6}$ alkyl and an optionally substituted $C_{1-6}$ haloalkyl; $R^2$ can be H or C(=O)$R^{2A}$; $R^{2A}$ can be selected from H, D, an optionally substituted $C_{1-30}$ alkyl, an optionally substituted $C_{2-30}$ alkenyl, an optionally substituted $C_{2-30}$ alkynyl, an optionally substituted $C_{3-30}$ cycloalkyl, an optionally substituted $C_{1-4}$ alkoxy and an optionally substituted $C_{1-8}$ haloalkyl; each $A^1$ can be independently $CR^4R^5$; each $R^4$ and each $R^5$ can be independently selected from H, D, halogen, an unsubstituted $C_{1-8}$ alkyl and an unsubstituted $C_{1-6}$ haloalkyl; and m can be 0 or 1.

In some embodiments, $B^1$ can be an optionally substituted 5-membered monocyclic heteroaryl. In other embodiments, $B^1$ can be an optionally substituted 6-membered monocyclic heteroaryl. The number of heteroatom present in the heteroaryl can vary. In some embodiments, the heteroaryl ring can include one heteroatom. In other embodiments, the heteroaryl ring can include two heteroatoms. In still other embodiments, the heteroaryl ring can include three heteroatoms. Examples of suitable heteroatoms include N (nitrogen), O (oxygen) and S (sulfur). In some embodiment, when two of the heteroatoms are N, the two Ns can share a bond.

In some embodiments, $B^1$ can be an optionally substituted 5-membered monocyclic heteroaryl selected from an optionally substituted furanyl, an optionally substituted furazanyl, an optionally substituted thiophenyl, an optionally substituted pyrrole, an optionally substituted oxazolyl, an optionally substituted 1,2,3-oxadiazolyl, an optionally substituted 1,2,4-oxadiazolyl, an optionally substituted 1,3,4-oxadiazolyl, an optionally substituted thiazolyl, an optionally substituted 1,2,3-thiadiazolyl, an optionally substituted 1,3,4-thiadiazolyl, an optionally substituted 1,2,4-thiadiazolyl, an optionally substituted imidazolyl, an optionally substituted pyrazolyl, an optionally substituted isoxazolyl, an optionally substituted isothiazolyl, an optionally substituted triazolyl and an optionally substituted tetrazolyl.

In some embodiments, $B^1$ can be a substituted 5-membered monocyclic heteroaryl selected from a substituted furanyl, a substituted furazanyl, a substituted thiophenyl, a substituted pyrrolyl, a substituted oxazolyl, a substituted 1,2,3-oxadiazolyl, a substituted 1,2,4-oxadiazolyl, a substituted 1,3,4-oxadiazolyl, a substituted thiazolyl, a substituted 1,2,3-thiadiazolyl, a substituted 1,3,4-thiadiazolyl, a substituted 1,2,4-thiadiazolyl, a substituted imidazolyl, a substituted pyrazolyl, a substituted isoxazolyl, a substituted isothiazolyl, a substituted triazolyl and a substituted tetrazolyl.

In some embodiments, $B^1$ can be an optionally substituted 5-membered monocyclic heteroaryl having one of the following structures:

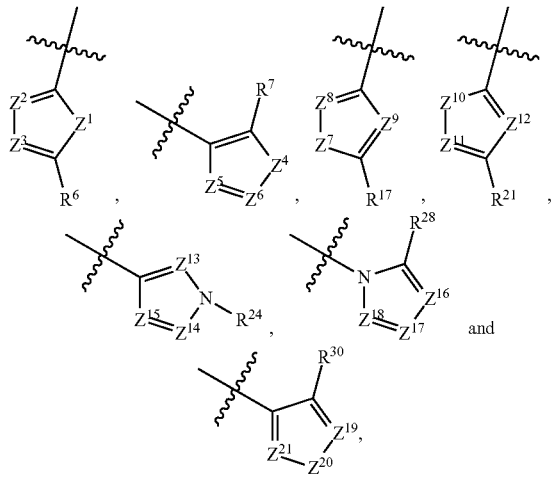

wherein: $Z^1$ can be O, S or $NR^8$; $Z^2$ can be $CR^9$ or N; $Z^3$ can be N or $CR^{10}$; $Z^4$ can be O, S or $NR^{11}$; $Z^5$ can be $CR^{12}$ or N; $Z^6$ can be N or $CR^{13}$; $Z^7$ can be O, S or $NR^{14}$; $Z^8$ can be $CR^{15}$ or N; $Z^9$ can be N or $CR^{16}$; L can be O, S or $NR^{18}$; $Z^{11}$ can be $CR^{19}$ or N; $Z^{12}$ can be N or $CR^{20}$; $Z^{13}$ can be $CR^{22}$ or N; $Z^{14}$ can be $CR^{23}$ or N; $Z^{15}$ can be N or $CR^{25}$; $Z^{16}$ can be N or $CR^{26}$; $Z^{17}$ can be N or $CR^{27}$; $Z^{18}$ can be N or $CR^{29}$; $Z^{19}$ can be N or $CR^{31}$; $Z^{20}$ can be O, S or $NR^{32}$; $Z^{21}$ can be N or $CR^{33}$; $R^6$, $R^7$, $R^{17}$, $R^{21}$, $R^{28}$ and $R^{30}$ can be each independently selected from H, D, halogen, hydroxy, $C_{1-4}$ alkoxy, $C_{1-8}$ alkyl, $C_{3-20}$ cycloalkyl, aryl, heteroaryl, heterocyclyl, $C_{1-6}$ haloalkyl, cyano, $C_{2-8}$ alkenyl, $C_{2-8}$ alkynyl, $C_{3-20}$ cycloalkenyl, aryl(alkyl), heteroaryl(alkyl), heterocyclyl(alkyl), acyl, thiocarbonyl, O-carbamyl, N-carbamyl, O-thiocarbamyl, N-thiocarbamyl, C-amido, N-amido, C-thioamido, N-thioamido, S-sulfonamido, N-sulfonamido, C-carboxy, O-carboxy, sulfenyl, sulfinyl, sulfonyl, haloalkoxy, an amino, a mono-substituted amino group and a di-substituted amino group, wherein each of the aforementioned substituents can be optionally substituted; and $R^8$, $R^{11}$, $R^{14}$, $R^{18}$, $R^{24}$ and $R^{32}$ are each independently selected from H, an optionally substituted $C_{1-6}$ alkyl, an optionally substituted aryl, an optionally substituted heteroaryl and an optionally substituted $C_{1-6}$ haloalkyl; and $R^9$, $R^{10}$, $R^{12}$, $R^{13}$, $R^{15}$, $R^{16}$, $R^{19}$, $R^{20}$, $R^{22}$, $R^{23}$, $R^{25}$ $R^{26}$, $R^{27}$, $R^{29}$, $R^{31}$ and $R^{33}$ are each independently selected from H, D, halogen, hydroxy, $C_{1-4}$ alkoxy, $C_{1-8}$ alkyl, $C_{3-20}$ cycloalkyl, aryl, heteroaryl, heterocyclyl, $C_{1-6}$ haloalkyl, cyano, $C_{2-8}$ alkenyl, $C_{2-8}$ alkynyl, $C_{3-20}$ cycloalkenyl, aryl(alkyl), heteroaryl(alkyl), heterocyclyl(alkyl), acyl, thiocarbonyl, O-carbamyl, N-carbamyl, O-thiocarbamyl, N-thiocarbamyl, C-amido, N-amido, C-thioamido, N-thioamido, S-sulfonamido, N-sulfonamido, C-carboxy, O-carboxy, sulfenyl, sulfinyl, sulfonyl, haloalkoxy, an amino, a mono-substituted amino group and a di-substituted amino group, wherein each of the aforementioned substituents can be optionally substituted.

In some embodiments, $B^1$ can be an optionally substituted 6-membered monocyclic heteroaryl selected from an optionally substituted pyridinyl, an optionally substituted pyrimidinyl, an optionally substituted pyrazinyl, an optionally substituted pyridazinyl, an optionally substituted 1,2,3-triazinyl, an optionally substituted 1,2,4-triazinyl, an optionally substituted 1,2,4,5-tetrazinyl and an optionally substituted 1,2,3,4-tetrazinyl.

In some embodiments, $B^1$ can be a substituted 6-membered monocyclic heteroaryl selected from a substituted pyridinyl, a substituted pyrimidinyl, a substituted pyrazinyl, a substituted pyridazinyl, a substituted 1,2,3-triazinyl, a substituted 1,2,4-triazinyl, a substituted 1,2,4,5-tetrazinyl and a substituted 1,2,3,4-tetrazinyl.

In some embodiments $B^1$ can be an optionally substituted 6-membered monocyclic heteroaryl having one of the following structures:

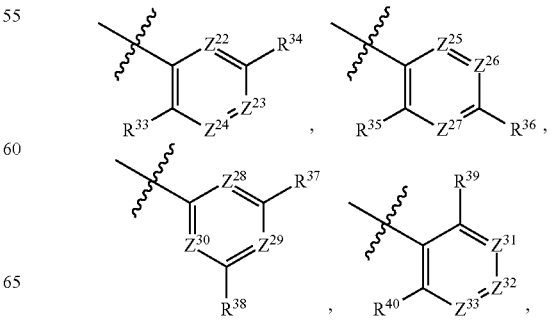

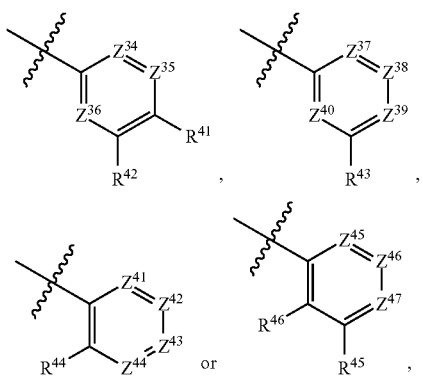

wherein: $Z^{22}$ can be $CR^{47}$ or N; $Z^{23}$ can be $CR^{48}$ or N; $Z^{24}$ can be $CR^{49}$ or N; $Z^{25}$ can be $CR^{50}$ or N; $Z^{26}$ can be $CR^{51}$ or N; $Z^{27}$ can be $CR^{52}$ or N; $Z^{28}$ can be $CR^{53}$ or N; $Z^{29}$ can be $CR^{54}$ or N; $Z^{30}$ can be $CR^{55}$ or N; $Z^{31}$ can be $CR^{56}$ or N; $Z^{32}$ can be $CR^{57}$ or N; $Z^{33}$ can be $CR^{58}$ or N; $Z^{34}$ can be $CR^{59}$ or N; $Z^{35}$ can be $CR^{60}$ or N; $Z^{36}$ can be $CR^{61}$ or N; $Z^{37}$ can be $CR^{62}$ or N; $Z^{38}$ can be $CR^{63}$ or N; $Z^{39}$ can be $CR^{64}$ or N; $Z^{40}$ can be $CR^{65}$ or N; $Z^{41}$ can be $CR^{66}$ or N; $Z^{42}$ can be $CR^{67}$ or N; $Z^{43}$ can be $CR^{68}$ or N; $Z^{44}$ can be $CR^{69}$ or N; $Z^{45}$ can be $CR^{70}$ or N; $Z^{46}$ can be $CR^{71}$ or N; $Z^{47}$ can be $CR^{72}$ or N; $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$ and $R^{46}$ can be each independently selected from H, D, halogen, hydroxy, $C_{1-4}$ alkoxy, $C_{1-8}$ alkyl, $C_{3-20}$ cycloalkyl, aryl, heteroaryl, heterocyclyl, $C_{1-6}$ haloalkyl, cyano, $C_{2-8}$ alkenyl, $C_{2-8}$ alkynyl, $C_{3-20}$ cycloalkenyl, aryl (alkyl), heteroaryl (alkyl), heterocyclyl(alkyl), acyl, thiocarbonyl, O-carbamyl, N-carbamyl, O-thiocarbamyl, N-thiocarbamyl, C-amido, N-amido, C-thioamido, N-thioamido, S-sulfonamido, N-sulfonamido, C-carboxy, O-carboxy, sulfenyl, sulfinyl, sulfonyl, haloalkoxy, an amino, a mono-substituted amino group and a di-substituted amino group, wherein each of the aforementioned substituents can be optionally substituted; and $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$ and $R^{72}$ can be each independently selected from H, D, halogen, hydroxy, $C_{1-4}$ alkoxy, $C_{1-8}$ alkyl, $C_{3-20}$ cycloalkyl, aryl, heteroaryl, heterocyclyl, $C_{1-6}$ haloalkyl, cyano, $C_{2-8}$ alkenyl, $C_{2-8}$ alkynyl, $C_{3-20}$ cycloalkenyl, aryl(alkyl), heteroaryl(alkyl), heterocyclyl(alkyl), acyl, thiocarbonyl, O-carbamyl, N-carbamyl, O-thiocarbamyl, N-thiocarbamyl, C-amido, N-amido, C-thioamido, N-thioamido, S-sulfonamido, N-sulfonamido, C-carboxy, O-carboxy, sulfenyl, sulfinyl, sulfonyl, haloalkoxy, an amino, a mono-substituted amino group and a di-substituted amino group, wherein each of the aforementioned substituents can be optionally substituted.

In some embodiments $B^1$ can be a 6-membered monocyclic heteroaryl having one of the following structures:

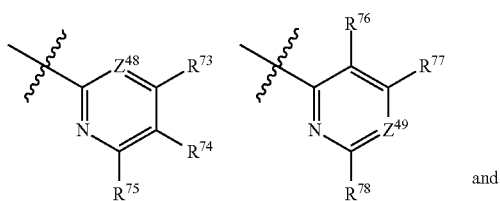

and

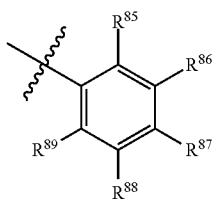

wherein: $Z^{48}$ can be $CR^{82}$ or N; $Z^{49}$ can be $CR^{83}$ or N; $Z^{50}$ can be $CR^{84}$ or N; $R^{73}$, $R^{74}$, $R^{75}$, $R^{76}$, $R^{77}$, $R^{78}$, $R^{79}$, $R^{80}$ and $R^{81}$ can be each independently selected from H, D, halogen, hydroxy, $C_{1-4}$ alkoxy, $C_{1-8}$ alkyl, $C_{3-20}$ cycloalkyl, aryl, heteroaryl, heterocyclyl, $C_{1-6}$ haloalkyl, cyano, $C_{2-8}$ alkenyl, $C_{2-8}$ alkynyl, $C_{3-20}$ cycloalkenyl, aryl(alkyl), heteroaryl(alkyl), heterocyclyl(alkyl), acyl, thiocarbonyl, O-carbamyl, N-carbamyl, O-thiocarbamyl, N-thiocarbamyl, C-amido, N-amido, C-thioamido, N-thioamido, S-sulfonamido, N-sulfonamido, C-carboxy, O-carboxy, sulfenyl, sulfinyl, sulfonyl, haloalkoxy, an amino, a mono-substituted amino group and a di-substituted amino group, wherein each of the aforementioned substituents can be optionally substituted; and $R^{82}$, $R^{83}$, and $R^{84}$ can be each independently selected from H, D, halogen, hydroxy, $C_{1-4}$ alkoxy, $C_{1-8}$ alkyl, $C_{3-20}$ cycloalkyl, aryl, heteroaryl, heterocyclyl, $C_{1-6}$ haloalkyl, cyano, $C_{2-8}$ alkenyl, $C_{2-8}$ alkynyl, $C_{3-20}$ cycloalkenyl, aryl (alkyl), heteroaryl(alkyl), heterocyclyl(alkyl), acyl, thiocarbonyl, O-carbamyl, N-carbamyl, O-thiocarbamyl, N-thiocarbamyl, C-amido, N-amido, C-thioamido, N-thioamido, S-sulfonamido, N-sulfonamido, C-carboxy, O-carboxy, sulfenyl, sulfinyl, sulfonyl, haloalkoxy, an amino, a mono-substituted amino group and a di-substituted amino group, wherein each of the aforementioned substituents can be optionally substituted.

In some embodiments $B^1$ can be an optionally substituted phenyl. In some embodiments the phenyl can be mono-substituted. In other embodiments the phenyl can be di-substituted. In still other embodiments the phenyl can be tri-substituted. In some embodiments the phenyl can be para-substituted. In some embodiments the phenyl can be ortho-substituted. In some embodiments the phenyl can be meta-substituted.

In some embodiments, $B^1$ can be an optionally substituted phenyl having the structure:

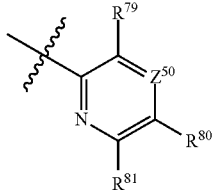

wherein: $R^{85}$, $R^{86}$, $R^{87}$, $R^{88}$ and $R^{89}$ can be independently selected from H, D, halogen, hydroxy, $C_{1-4}$ alkoxy, $C_{1-8}$ alkyl, $C_{3-20}$ cycloalkyl, aryl, heteroaryl, heterocyclyl, $C_{1-6}$ haloalkyl, cyano, $C_{2-8}$ alkenyl, $C_{2-8}$ alkynyl, $C_{3-20}$ cycloalkenyl, aryl(alkyl), heteroaryl(alkyl), heterocyclyl(alkyl), acyl, thiocarbonyl, O-carbamyl, N-carbamyl, O-thiocarbamyl, N-thiocarbamyl, C-amido, N-amido, C-thioamido, N-thioamido, S-sulfonamido, N-sulfonamido, C-carboxy, O-carboxy, sulfenyl, sulfinyl, sulfonyl, haloalkoxy, an amino, a mono-substituted amino group and a di-substituted amino group, wherein each of the aforementioned substituents can be optionally substituted.

In some embodiments, $R^{87}$ cannot be an amino group. In other embodiments, $R^{87}$ cannot be a mono-substituted amino group. In some embodiments, $R^{87}$ cannot be a hydroxy group. In some embodiments, $R^{87}$ cannot be a C-carboxy.

In some embodiments, one or more of $R^{85}$, $R^{86}$, $R^{87}$, $R^{88}$ and/or $R^{89}$ cannot be a substituted or an unsubstituted amino group. In other embodiments, one or more of $R^{85}$, $R^{86}$, $R^{87}$, $R^{88}$ and/or $R^{89}$ cannot be a substituted or an unsubstituted $C_{1-4}$ alkyl group (such as methyl, ethyl, or tut-butyl). In further embodiments, one or more of $R^{85}$, $R^{86}$, $R^{87}$, $R^{88}$ and/or $R^{89}$ cannot be a substituted or an unsubstituted acyl group. In still further embodiments, one or more of $R^{85}$, $R^{86}$, $R^{87}$, $R^{88}$ and/or $R^{89}$ cannot be a substituted or an unsubstituted $C_{1-4}$ alkoxy. In yet further embodiments, one or more of $R^{85}$, $R^{86}$, $R^{87}$, $R^{88}$ and/or $R^{89}$ cannot be a substituted or an unsubstituted $C_{1-6}$ haloalkyl. In yet other embodiments, one or more of $R^{85}$, $R^{86}$, $R^{87}$, $R^{88}$ and/or $R^{89}$ cannot be a halogen (such as F, Cl or I). In some embodiments, one or more of $R^{85}$, $R^{86}$, $R^{87}$, $R^{88}$ and/or $R^{89}$ cannot be a hydroxy.

In some embodiments, B can be a phenyl having the structure:

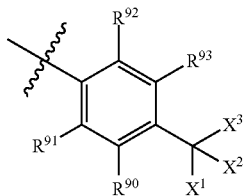

wherein: $R^{90}$, $R^{91}$, $R^{92}$ and $R^{93}$ can be each independently selected from H, D, halogen, hydroxy, $C_{1-4}$ alkoxy, $C_{1-4}$ alkyl, $C_{3-20}$ cycloalkyl, aryl, heteroaryl, heterocyclyl, $C_{1-6}$ haloalkyl, cyano, $C_{2-8}$ alkenyl, $C_{2-8}$ alkynyl, $C_{3-20}$ cycloalkenyl, aryl(alkyl), heteroaryl(alkyl), heterocyclyl(alkyl), acyl, thiocarbonyl, O-carbamyl, N-carbamyl, O-thiocarbamyl, N-thiocarbamyl, C-amido, N-amido, C-thioamido, N-thioamido, S-sulfonamido, N-sulfonamido, C-carboxy, O-carboxy, sulfenyl, sulfinyl, sulfonyl, haloalkoxy, an amino, a mono-substituted amino group and a di-substituted amino group, wherein each of the aforementioned substituents can be optionally substituted; and $X^1$, $X^2$ and $X^3$ can be each independently selected from H, D, halogen, hydroxy, $C_{1-4}$ alkoxy, $C_{1-8}$ alkyl, $C_{3-20}$ cycloalkyl, aryl, heteroaryl, heterocyclyl, $C_{1-6}$ haloalkyl, cyano, $C_{2-8}$ alkenyl, $C_{2-8}$ alkynyl, $C_{3-20}$ cycloalkenyl, aryl(alkyl), heteroaryl(alkyl), heterocyclyl(alkyl), acyl, thiocarbonyl, O-carbamyl, N-carbamyl, O-thiocarbamyl, N-thiocarbamyl, C-amido, N-amido, C-thioamido, N-thioamido, S-sulfonamido, N-sulfonamido, C-carboxy, O-carboxy, sulfenyl, sulfinyl, sulfonyl, haloalkoxy, an amino, a mono-substituted amino group and a di-substituted amino group, wherein each of the aforementioned substituents can be optionally substitute.

In some embodiments $X^1$, $X^2$ and $X^3$ can be each optionally substituted $C_{1-8}$ alkyl. Suitable $C_{1-8}$ alkyl groups are described herein. In some embodiments $X^1$, $X^2$ and $X^3$ are each methyl. In other embodiments at least one of $X^1$, $X^2$ and $X^3$ can be halo. In still other embodiments two of $X^1$, $X^2$ and $X^3$ are halo. In yet still other embodiments $X^1$, $X^2$ and $X^3$ can be each halo. When $X^1$, $X^2$ and/or $X^3$ are halo, the halo can be fluoro.

A variety of substituents can be present when $B^1$ is substituted. As used herein, when $B^1$ is "substituted", $B^1$ includes at least one substituent in addition to -$(A^1)_m$-$NR^1R^2$. Likewise, when $B^1$ is "unsubstituted", $B^1$ includes only -$(A^1)_m$-$NR^1R^2$. In some embodiments, $B^1$ can be substituted with one or more substituents. In some embodiments, $B^1$ can be substituted with one substituent.

In some embodiments, $B^1$ can be substituted with one or more substituents selected from D, halogen, hydroxy, $C_{1-4}$ alkoxy, $C_{1-8}$ alkyl, $C_{3-20}$ cycloalkyl, aryl, heteroaryl, heterocyclyl, $C_{1-6}$ haloalkyl, cyano, $C_{2-8}$ alkenyl, $C_{2-8}$ alkynyl, $C_{3-20}$ cycloalkenyl, aryl(alkyl), heteroaryl(alkyl), heterocyclyl(alkyl), acyl, thiocarbonyl, O-carbamyl, N-carbamyl, O-thiocarbamyl, N-thiocarbamyl, C-amido, N-amido, C-thioamido, N-thioamido, S-sulfonamido, N-sulfonamido, C-carboxy, O-carboxy, sulfenyl, sulfinyl, sulfonyl, haloalkoxy, an amino, a mono-substituted amino group and a di-substituted amino group, wherein each of the aforementioned substituents can be optionally substituted. When a substituent on $B^1$ is optionally substituted, that substituent may be unsubstituted or substituted with one or more substituents as understood by those of skill in the art, and provided herein. In some embodiments, a substituent on $B^1$ can itself be substituted.

In some embodiments, $B^1$ can be substituted with one or more substituents selected from D, halogen, hydroxy, $C_{1-4}$ alkoxy, $C_{1-8}$ alkyl, aryl, $C_{1-6}$ haloalkyl, acyl, C-amido, N-amido, C-carboxy, O-carboxy, an amino, a mono-substituted amino group and a di-substituted amino group, wherein each of the aforementioned substituents can be optionally substituted. In some embodiments, $B^1$ can be substituted with up to two substituents of this paragraph.

In some embodiments, $B^1$ can be substituted with one or more substituents selected from halogen, hydroxy, $C_{1-4}$ alkoxy, $C_{1-8}$ alkyl and $C_{1-6}$ haloalkyl. In further embodiments, $B^1$ can be substituted with up to two substituents of this paragraph.

In some embodiments, $B^1$ can be substituted with one or more substituents selected from O-thiocarbamyl, N-thiocarbamyl, C-thioamido, N-thioamido, S-sulfonamido, N-sulfonamido, sulfenyl, sulfinyl and sulfonyl, wherein each of the aforementioned substituents can be optionally substituted. In further embodiments, $B^1$ can be substituted with one or two substituents of this paragraph.

In some embodiments, $B^1$ can be substituted with an N-containing substituent. Suitable substituents of this paragraph include heterocyclyl, O-carbamyl, N-carbamyl, O-thiocarbamyl, N-thiocarbamyl, C-amido, N-amido, C-thioamido, N-thioamido, S-sulfonamido, N-sulfonamido, an amino, a mono-substituted amino group and a di-substituted amino group, wherein each of the aforementioned substituents can be optionally substituted. In further embodiments, $B^1$ can be substituted with one or two substituents of this paragraph.

In some embodiments, $B^1$ can be substituted with D. In other embodiments, $B^1$ can be substituted with a halo. For example, $B^1$ can be substituted with F (fluoro) or Cl (chloro). In yet still other embodiments, $B^1$ can be substituted with hydroxy. In some embodiments, when $B^1$ is substituted by a hydroxy, an amino, a mono-substituted amino or a thiol, $B^1$ includes all tautomers.

In some embodiments, $B^1$ can be substituted with a substituted $C_{1-8}$ alkyl. In other embodiments, $B^1$ can be substituted with an unsubstituted $C_{1-8}$ alkyl. Suitable substituted and unsubstituted $C_{1-8}$ alkyl groups include, methyl, ethyl, n-propyl, iso-propyl, n-butyl, iso-butyl, tert-butyl, pentyl (straight and branched), hexyl (straight and branched), heptyl (straight and branched) and octyl (straight and branched).

In some embodiments, $B^1$ can be substituted with a substituted or an unsubstituted $C_{2-8}$ alkenyl. In some embodiments, $B^1$ can be substituted with a substituted or an unsubstituted $C_{2-4}$ alkenyl. In some embodiments, $B^1$ can be substituted with a substituted or an unsubstituted $C_{2-8}$ alkynyl. In some embodiments, $B^1$ can be substituted with a substituted or an unsubstituted $C_{2-4}$ alkynyl. Suitable substituents of this paragraph include, but are not limited to, allyl, propargyl and isoprenyl.

In some embodiments, $B^1$ can be substituted with a substituted or an unsubstituted cyclic group. In some embodiments, $B^1$ can be substituted with a substituted or an unsubstituted $C_{3-20}$ cycloalkyl. In some embodiments, $B^1$ can be substituted with a substituted or unsubstituted $C_{3-4}$ cycloalkyl. In other embodiments, $B^1$ can be substituted with a substituted or unsubstituted cyclohexyl. The cycloalkyl group can be a mono-cyclic cycloalkyl or a multi-cyclic cycloalkyl group (such as a bi-cyclic cycloalkyl). In some embodiments, $B^1$ can be substituted with substituted or unsubstituted $C_{3-20}$ cycloalkenyl. Similar to a cycloalkyl group, a cycloalkenyl group can be a mono-cyclic cycloalkenyl or a multi-cyclic cycloalkenyl group (such as a bi-cyclic cycloalkenyl). As described herein, when the cycloalkyl and/or cycloalkenyl group includes more than 1 ring, the rings can be joined together in a fused, spiro or bridged fashion. In some embodiments, a cycloalkyl and/or a cycloalkenyl can include 3 to 10 ring carbon atom(s). In other embodiments, a cycloalkyl and/or a cycloalkenyl can include 3 to 6 ring carbon atom(s).

Other examples of suitable cyclic groups include aryl, heteroaryl and heterocyclyl groups. In some embodiments, $B^1$ can be substituted with a substituted or an unsubstituted $C_{6-20}$ aryl. Examples of $C_{6-20}$ aryl groups are described herein. In some embodiments, $B^1$ can be substituted with a substituted or unsubstituted phenyl. The phenyl ring can be substituted with 1 substituent group, 2 substituent groups or 3 or more substituents. The substituent group(s) can be present at the ortho, meta and/or para position(s). In some embodiments, $B^1$ can be substituted with a substituted or unsubstituted naphthyl.

In some embodiments, $B^1$ can be substituted with a substituted or an unsubstituted heteroaryl. The number of rings of a heteroaryl group can vary. For example, in some embodiments, $B^1$ can be substituted with a substituted or an unsubstituted mono-cyclic heteroaryl. The mono-cyclic heteroaryl can include 5 or 6 ring atoms. In still other embodiments, $B^1$ can be substituted with a substituted or an unsubstituted multi-cyclic heteroaryl (for example, a substituted bi-cyclic heteroaryl). The number of ring atoms of a multi-cyclic heteroaryl can vary. For example, a multi-cyclic heteroaryl can include 9 or 10 ring atoms.

In some embodiments, $B^1$ can be substituted with a substituted or an unsubstituted heterocyclyl. As with a heteroaryl group, the number of rings of a heterocyclyl group can vary. In some embodiments, $B^1$ can be substituted with a substituted or an unsubstituted mono-cyclic heterocyclyl. In still other embodiments, $B^1$ can be substituted with a substituted or an unsubstituted bi-cyclic heterocyclyl. A mono-cyclic heterocyclyl and a bi-cyclic heterocyclyl can include a various number of ring atoms. A mono-cyclic heterocyclyl can include 5 to 6 ring atoms, and a bi-cyclic heterocyclyl can include 9 to 10 ring atoms.

As described herein, a linker can be used to connect a cyclic group to $B^1$. In some embodiments, $B^1$ can be substituted with a substituted or an unsubstituted aryl($C_{1-6}$ alkyl). For example, in some embodiments, $B^1$ can be substituted with a substituted or an unsubstituted benzyl. The phenyl ring of a benzyl group can be substituted with 1 substituent, 2 substituents, 3 substituents or 3 or more substituents.

In some embodiments, $B^1$ can be substituted with a substituted or an unsubstituted heteroaryl($C_{1-6}$ alkyl). The heteroaryl ring can be a substituted or an unsubstituted mono-cyclic heteroaryl or substituted or an unsubstituted multi-cyclic heteroaryl (such as a bi-cyclic heteroaryl). In still other embodiments, $B^1$ can be substituted with a substituted or an unsubstituted heterocyclyl($C_{1-6}$ alkyl). The number of rings of the heterocyclyl or a heterocyclyl($C_{1-6}$ alkyl) can vary. For example, in some embodiments, $B^1$ can be substituted with substituted or an unsubstituted mono-cyclic heterocyclyl($C_{1-6}$ alkyl). In still other embodiments, $B^1$ can be substituted with a substituted multi-cyclic heterocyclyl($C_{1-6}$ alkyl), for example, a substituted bi-cyclic heterocyclyl($C_{1-6}$ alkyl). In yet still other embodiments, $B^1$ can be substituted with an unsubstituted multi-cyclic heterocyclyl($C_{1-6}$ alkyl), for example, an unsubstituted bi-cyclic heterocyclyl($C_{1-6}$ alkyl). As described herein, the number of ring atoms of a heteroaryl($C_{1-6}$ alkyl) and/or a heterocyclyl ($C_{1-6}$ alkyl) can also vary. In some embodiments, a heteroaryl($C_{1-6}$ alkyl) and/or a heterocyclyl($C_{1-6}$ alkyl) can include 5 or 6 ring atoms. In other embodiments, a heteroaryl($C_{1-6}$ alkyl) and/or a heterocyclyl($C_{1-6}$ alkyl) can include 9 or 10 ring atoms.

In some embodiments, $B^1$ can be substituted with a substituted or an unsubstituted $C_{1-6}$ haloalkyl. Examples of suitable $C_{1-6}$ haloalkyls include, but are not limited to, $CF_3$, $CHF_2$, $CH_2F$, $CH_2CF_3$, $CH_2CHF_2$ and $CH_2CH_2F$.

In some embodiments, $B^1$ can be substituted with a substituted sulfonyl. In other embodiments, $B^1$ can be substituted with an unsubstituted sulfonyl. In some embodiments, $B^1$ can be substituted with $SO_2R^{++}$, wherein $R^{++}$ can be hydrogen, an optionally substituted $C_{1-6}$ alkyl, an optionally substituted $C_{2-8}$ alkenyl, an optionally substituted $C_{3-20}$ cycloalkyl, an optionally substituted mono-cyclic aryl, an optionally substituted mono-cyclic heteroaryl or an optionally substituted mono-cyclic heterocyclyl. In other embodiments, $B^1$ can be substituted with $SO_2R^{++}$, wherein $R^{++}$ can be an unsubstituted $C_{1-6}$ alkyl, an unsubstituted $C_{2-8}$ alkenyl or an unsubstituted $C_{3-20}$ cycloalkyl. In some embodiments, $B^1$ can be substituted with $SO_2CH_3$.

In some embodiments, $R^1$ can be H. In other embodiments, $R^1$ can be D. In still other embodiments, $R^1$ can be a substituted $C_{1-6}$ alkyl. In yet still other embodiments, $R^1$ can be an unsubstituted $C_{1-6}$ alkyl. For example, $R^1$ can be methyl. In another example, $R^1$ can be ethyl. Other examples of $C_{1-6}$ alkyl groups include n-propyl, iso-propyl, n-butyl, iso-butyl, tert-butyl, pentyl (straight and branched) and hexyl (straight and branched). In some embodiments, $R^1$ can be a substituted $C_{1-6}$ haloalkyl. In other embodiments, $R^1$ can be an unsubstituted $C_{1-6}$ haloalkyl. Examples of suitable $C_{1-6}$ haloalkyls include, but are not limited to, $CF_3$, $CH_2CF_3$, $CH_2CHF_2$ and $CH_2CH_2F$.

In some embodiments, $R^2$ can be H. When $R^2$ is H, $NR^1R^2$ of Formula (I) can be an amino or a mono-substituted amine group that can be attached to $B^1$ directly or through an optionally substituted methylene group. In some embodiments, $NR^1R^2$ of Formula (I) can be an amino group directly attached to $B^1$. In other embodiments, $NR^1R^2$ can be a mono-substituted amine group directly attached to $B^1$. In still other embodiments, an amino group can be attached to $B^1$ through an optionally substituted methylene. In yet still other embodiments, $NR^1R^2$ can be a mono-substituted group attached to $B^1$ through an optionally substituted methylene.

In some embodiments, $R^2$ can be $C(=O)R^{2A}$. When $R^2$ is $C(=O)R^{2A}$, $NR^1R^2$ of Formula (I) can be an optionally substituted amido group that can be attached to $B^1$ directly or through an optionally substituted methylene group. In some embodiments, $NR^1R^2$ can be an amido group directly attached to $B^1$. In other embodiments, the amido group can be attached to $B^1$ through a methylene group. The methylene group can be substituted or unsubstituted and can include one or more deuteriums.

When $R^2$ is $C(=O)R^{2A}$, $R^{2A}$ can be a variety of groups. In some embodiments, $R^{2A}$ can be H. In other embodiments, $R^{2A}$ can be D. In still other embodiments, $R^{2A}$ can be a substituted $C_{1-30}$ alkyl. In yet still other embodiments, $R^{2A}$ can be an unsubstituted $C_{1-30}$ alkyl. The alkyl group can be a long alkyl having 1 to 30 carbons, a medium alkyl having 1 to 12 carbon atoms or a lower alkyl having 1 to 6 carbon atoms. Examples of lower alkyl groups include, methyl, ethyl, n-propyl, iso-propyl, n-butyl, iso-butyl, a tert-butyl, pentyl (straight and branched) and hexyl (straight and branched). In some embodiments, $R^{2A}$ can be an unsubstituted alkyl having 8 to 26 carbon atoms. Examples of unsubstituted $C_{1-30}$ alkyls include, but are not limited to, $-(CH_2)_6CH_3$, $-(CH_2)_8CH_3$, $-(CH_2)_{10}CH_3$, $-(CH_2)_{12}CH_3$, $-(CH_2)_{14}CH_3$, $-(CH_2)_{16}CH_3$, $-(CH_2)_{18}CH_3$, $-(CH_2)_{20}CH_3$, $-(CH_2)_{22}CH_3$ and $-(CH_2)_{24}CH_3$.

In some embodiments, $R^{2A}$ can be a substituted $C_{2-30}$ alkenyl. In other embodiments, $R^{2A}$ can be an unsubstituted $C_{2-30}$ alkenyl. In still other embodiments, $R^{2A}$ can be a substituted $C_{2-30}$ alkynyl. In yet still other embodiments, $R^{2A}$ can be an unsubstituted $C_{2-30}$ alkynyl. Similar to alkyls, alkenyls and alkynyls can be a long alkenyl and/or alkynyl having 2 to 30 carbons, a medium alkenyl and/or alkynyl having 2 to 12 carbons, or a lower alkenyl and/or alkynyl having 2 to 6 carbon atoms. In some embodiments, $R^{2A}$ can be an unsubstituted alkenyl having 14 to 22 carbon atoms. Examples of unsubstituted $C_{2-30}$ alkenyls include, but are not limited to, $(CH_2)_7CH=CH(CH_2)_3CH_3$, $-(CH_2)_7CH=CHCH_2CH=CH(CH_2)_4CH_3$, $-(CH_2)_7CH=CH(CH_2)_7CH_3$, $(CH_2)_7CH=CHCH_2CH=CH(CH_2)_4CH_3$, $-(CH_2)_7CH=CH(CH_2)_7CH_3$, $-(CH_2)_7CH=CHCH_2CH=CHCH_2CH=CHCH_2CH_3$, $-(CH_2)_9CH=CH(CH_2)_5CH_3$, $-(CH_2)_3CH=CHCH_2CH=CHCH_2CH=CHCH_2CH=CH(CH_2)_4CH_3$, $-(CH_2)_{11}CH=CH(CH_2)_7CH_3$, $-(CH_2)_3CH=CHCH_2CH=CHCH_2CH=CHCH_2CH=CHCH_2CH_3$, $-(CH_2)_4CH=CHCH(CH_3)_2$ and $-(CH_2)_2CH=CHCH_2CH=CHCH_2CH=CHCH_2CH=CHCH_2CH=CHCH_2CH_3$.

In some embodiments, $R^{2A}$ can be the aliphatic tail of a saturated or an unsaturated fatty acid. As an example, $R^{2A}$ can be the aliphatic tail of caprylic acid (HOO$\underline{C}$(*CH₂*)₆*CH₃*). In this example of caprylic acid, the aliphatic tail is bolded and italicized. When the saturated or an unsaturated fatty acid becomes part of a compound of Formula (I), the carbon of the carboxylic acid of the saturated or an unsaturated fatty acid becomes the carbon that is bold and underlined carbon of $\underline{C}(=O)R^{2A}$. For example, when $R^{2A}$ is the aliphatic tail of caprylic acid, the compound of Formula (I) can have the following structure:

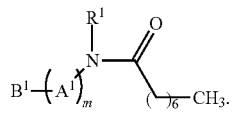

A non-limiting list of suitable saturated or an unsaturated fatty acids are myristoleic acid, palmitoleic, sapienic acid, linoleic acid, oleic acid, linoleiaidic acid, elaidic acid, alpha-linolenic acid, vaccenic acid, arachidonic acid, erucic acid, eicosapentaenoic acid, (E)-8-methylnon-6-enoic acid, docosahexaenoic acid, caprylic acid, capric acid, lauric acid, myristic acid, palmitic acid, stearic acid, arachidic acid, behenic acid, lignoceric acid and cerotic acid.

Cyclic groups can also be present at $R^{2A}$. In some embodiments, $R^{2A}$ can be a substituted $C_{3-30}$ cycloalkyl. In other embodiments, $R^{2A}$ can be an unsubstituted $C_{3-30}$ cycloalkyl. The number of carbon ring atoms of a cycloalkyl can vary. In some embodiments, the number of carbon ring atoms of a cycloalkyl can be 3 to 30, 3 to 20, 3 to 10, 3 to 8 or 3 to 6. The number rings of a cycloalkyl can also vary. In some embodiments, a cycloalkyl can be mono-cyclic. In other embodiments, a cycloalkyl can be bi-cyclic or tri-cyclic. As described herein, the rings of a multi-cyclic cycloalkyl can be joined together to form fused ring system, a bridged ring system and/or spiro-connected ring system.

In some embodiments, $R^{2A}$ can be a substituted $C_{1-4}$ alkoxy. In other embodiments, $R^{2A}$ can be an unsubstituted $C_{1-4}$ alkoxy. Examples of suitable $C_{1-4}$ alkoxy include, but are not limited to, methoxy, ethoxy, iso-propoxy, isopropoxy and tert-butoxy.

In some embodiments, $R^{2A}$ can be a substituted $C_{1-8}$ haloalkyl. In other embodiments, $R^{2A}$ can be an unsubstituted $C_{1-8}$ haloalkyl. Examples of suitable $C_{1-8}$ haloalkyls include, but are not limited to, $CF_3$, $CHF_2$, $CH_2F$, $CH_2CF_3$, $CH_2CHF_2$ and $CH_2CH_2F$.

As provided herein, a compound of Formula (I) can include a linker group between $B^1$ and $NR^1R^2$ or the $NR^1R^2$ group can be connected directly to $B^1$. In some embodiments, m can be 0. In other embodiments, m can be 1.

In some embodiments, the linker group can be represented by $A^1$, wherein $A^1$ can be $CR^4R^5$. In some embodiments, $R^4$ can be H. In other embodiments, $R^4$ can be D. In still other embodiments, $R^4$ can be an unsubstituted $C_{1-8}$ alkyl. In some embodiments, $R^4$ can be an unsubstituted $C_{1-6}$ haloalkyl, such as $CF_3$, $CHF_2$ or $CH_2F$. In some embodiments, $R^5$ can be H. In other embodiments, $R^5$ can be D. In other embodiments, $R^5$ can be an unsubstituted $C_{1-8}$ alkyl. In some embodiments, $R^5$ can be an unsubstituted $C_{1-6}$ haloalkyl, such as $CF_3$, $CHF_2$ or $CH_2F$. In some embodiments, $R^4$ and $R^5$ can be taken together to form an optionally substituted $C_{3-6}$ cycloalkyl. In some embodiments, one of $R^4$ and $R^5$ can be H, and the other of $R^4$ and $R^5$ can be an unsubstituted $C_{1-8}$ alkyl or an unsubstituted $C_{1-6}$ haloalkyl. In other embodiments, $R^4$ and $R^5$ can be independently an unsubstituted $C_{1-8}$ alkyl or an unsubstituted $C_{1-6}$ haloalkyl. In some embodiments, at least one of $R^4$ and $R^5$ can be D. In some embodiments, $R^4$ and $R^5$ each can be H.

In some embodiments, $B^1$ can be substituted by F, Cl, an unsubstituted $C_{1-8}$ alkyl, and/or an unsubstituted $C_{1-6}$ haloalkyl, $R^1$ can be H or $CH_3$, and $R^2$ can be H. In some embodiments, $B^1$ can be substituted by F, Cl, an unsubstituted $C_{1-8}$ alkyl, and/or an unsubstituted $C_{1-6}$ haloalkyl, $R^1$ can be H or $CH_3$, and $R^2$ can be $C(=O)R^{2A}$. In some embodiments, $B^1$ can be substituted by F, Cl, an unsubstituted $C_{1-8}$ alkyl, and/or an unsubstituted $C_{1-6}$ haloalkyl, $R^1$ can be H or $CH_3$, and $R^2$ can be $C(=O)R^{2A}$, wherein $R^{2A}$ can be an unsubstituted $C_{1-8}$ alkyl or an unsubstituted $C_{2-8}$ alkenyl. In some embodiments, $B^1$ can be substituted by F, Cl, an unsubstituted $C_{1-8}$ alkyl, an unsubstituted $C_{1-6}$ and/or haloalkyl, $R^1$ can be H or $CH_3$, and $R^2$ can be $C(=O)R^{2A}$, wherein $R^{2A}$ can be an unsubstituted $C_{8-30}$ alkyl or an unsubstituted $C_{8-30}$ alkenyl.

As described herein, the number of substituent groups present on a substituted $R^1$, $R^{2A}$, $R^4$ and/or $R^5$ group can vary. In some embodiments, the number of substituent groups present on a substituted $R^1$, $R^{2A}$, $R^4$ and/or $R^5$ can be 1. In some embodiments, the number of substituent groups present on a substituted $R^1$, $R^{2A}$, $R^4$ and/or $R^5$ can be up to 2. In some embodiments, the number of substituent groups present on a substituted $R^1$, $R^{2A}$, $R^4$ and/or $R^5$ can be up to 3. In some embodiments, the number of substituent groups present on a substituted $R^1$, $R^{2A}$, $R^4$ and/or $R^5$ can be 4 or more. When more than 1 substituent group is present, a group can be the same as at least one other group. Additionally and/or in the alternative, when more than 1 substituent group is present, a group can be different from at least one other group.

A non-limiting list of examples of compounds of Formula (I), or a pharmaceutically acceptable salt, include:

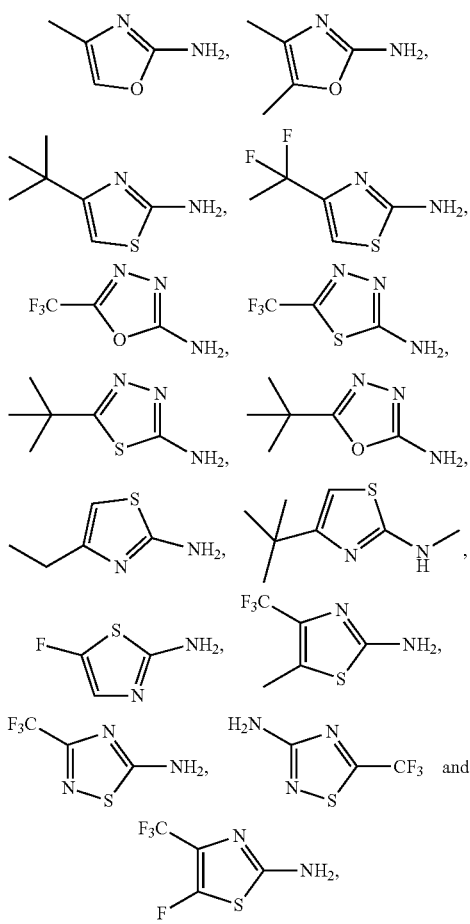

or a pharmaceutically acceptable salt of any of the foregoing.

Additional examples of compounds of Formula (I), or a pharmaceutically acceptable salt, include the following:

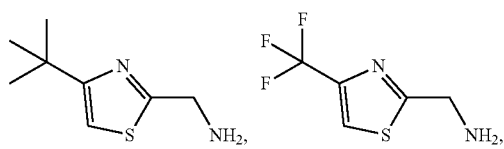

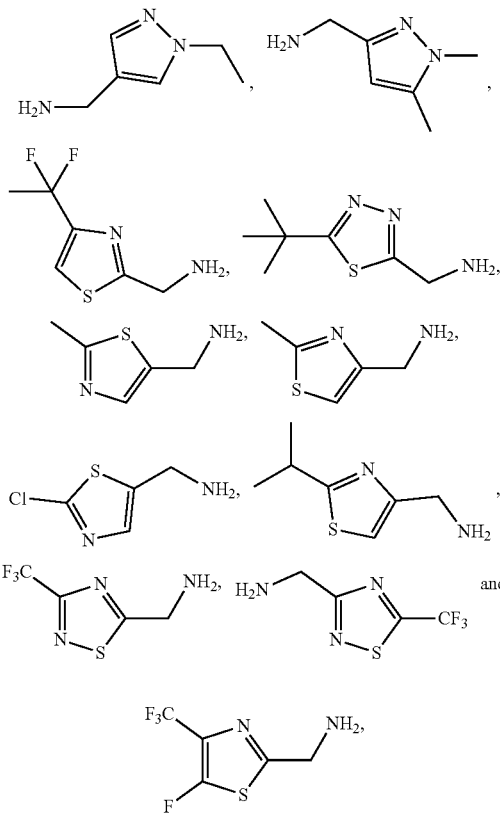

or a pharmaceutically acceptable salt of any of the foregoing.

Further examples of compounds of Formula (I), or a pharmaceutically acceptable salt, include the following:

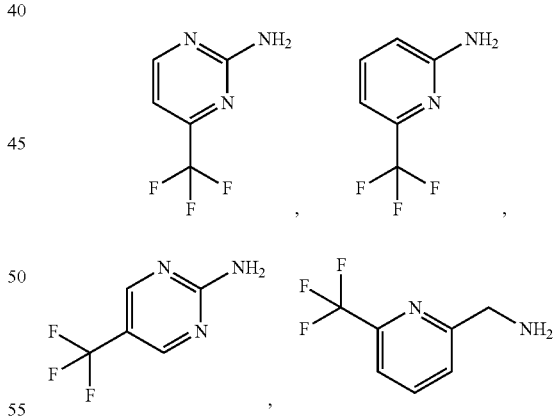

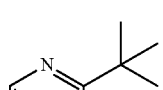

or a pharmaceutically acceptable salt of any of the foregoing.

Yet further examples of compounds of Formula (I), or a pharmaceutically acceptable salt, include the following:

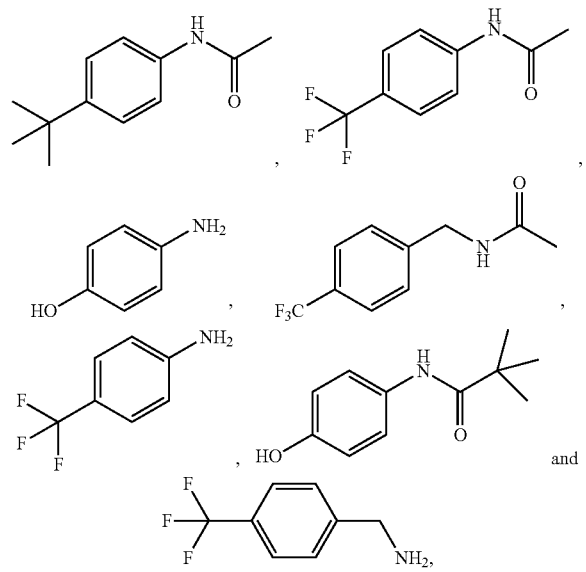

or a pharmaceutically acceptable salt of any of the foregoing.

In some embodiments, a compound of Formula (I), or a pharmaceutically acceptable salt thereof, cannot be one or more of the compounds provided in one or more of the following references if a compound provided in a reference is determined to fall within the scope of Formula (I), or a pharmaceutically acceptable salt thereof: WO 2013/059648 (filed 19 Oct. 2012); WO 2004/054582 (filed 19 Nov. 2003); WO 2004/063161 (filed 19 Dec. 2003); U.S. Patent Publication No. 2006/002545 (filed 20 Jun. 2005); U.S. Pat. No. 4,508,911, (filed 14 Feb. 1984); Lohitha, et al., *RGUHS Journal of Pharmaceutical Sciences* (2011) 1(1):69-78; U.S. Pat. No. 6,638,933 (filed 8 Apr. 2002); Cocco et al., *European Journal of Medicinal Chemistry* (2003) 38:513-518; Fresno, et al., Adamantyl Analogues of Paracetamol as Potent Analgesic Drugs via Inhibition of TRPA1, *PLOS ONE* (Dec. 1, 2014) 9(12) e113841:1-16; Sinning et al. *J. Med. Chem.* (2008) 51(24):7800-7805; European Patent Application Publication No. 0 402 752 (filed Jun. 6, 1990); German Patent Publication No. 102 61 091 A1 (to GRUENENTHAL GMBH); Belgian Patent Publication No. 893479 (10 Jun. 1982 to CORTIAL); Raju, et al. *World Journal of Pharmacy and Pharmaceutical Sciences* (2015) 4(5): 1815-1821; Madjavi et al. *International Journal of Pharmaceutical Sciences and Nanotechnology* (2013) 5(4): 1879-1884; Zhang et al., *Bioorganic and Medicinal Chemistry Letters* (2006) 16:2013-2016; Max et al., *New England Journal of Medicine* (1992) 326:1250-1256; Johnson et al., *British Medical Journal* (2003) 326:748-750; Freynhagen et al., *Pain* (2005) 115:254-263; U.S. Pat. No. 6,638,933, (filed 8 Apr. 2002); U.S. Patent Publication No. 2004/0209959 (filed 16 Jul. 2002); Sippy et al., *Bioorganic and Medicinal Chemistry Letters* (2009) 19:1682-1685; Decker et al., *Expert Opinion on Investigational Drugs* (2001) 16:1819-1830.

In some embodiments, the compound of Formula (I) cannot be N-(4-hydroxyphenyl)acetamide. In other embodiments, the compound of Formula (I) cannot be 2-(2-methylthiazol-4-yl)ethan-1-amine. In still other embodiments, the compound of Formula (I) cannot be β-(6-methyl-2-pyridyl)isopropylamine, β-(2-pyridyl)isopropylamine. In further embodiments, neither $R^4$ nor $R^5$ can be methyl. In still further embodiments, $B^1$ cannot be pyridyl. In yet further embodiments, $B^1$ cannot be pyridyl substituted by an unsubstituted $C_{1-8}$ alkyl. In other embodiments, $B^1$ cannot be thiazolyl. In yet other embodiments, $B^1$ cannot be thiazolyl substituted by an aryl. In some embodiments, $B^1$ cannot be thiazolyl substituted by a substituted or an unsubstituted $C_{1-8}$ alkyl.

In some embodiments, when $B^1$ is a substituted phenyl, $B^1$ cannot be substituted by an optionally substituted C-carboxy. In some embodiments, when $B^1$ is substituted phenyl, $B^1$ cannot be substituted by a carboxylic acid (—COOH). In some embodiments, $B^1$ cannot be substituted by an optionally substituted N-imine. In some embodiments, when $B^1$ is a substituted phenyl, $B^1$ cannot be substituted by an optionally substituted thiourea. In some embodiments, when $B^1$ is a substituted phenyl and when m is 0, $B^1$ cannot be substituted by a para-halo. In some embodiments, when $B^1$ is a substituted phenyl, $B^1$ cannot be substituted by a para-C-carboxy. In some embodiments, when $B^1$ is a substituted or an unsubstituted phenyl or a substituted or an unsubstituted thiophenyl, $R^{2A}$ cannot be a $C_{1-30}$ alkyl substituted by a cyano. In some embodiments, when $B^1$ is a substituted thiophenyl, $B^1$ cannot be substituted by an optionally substituted C-carboxy. In some embodiments, when m is 0, $B^1$ cannot be substituted by a $C_{1-8}$ alkyl group substituted with an amino, an optionally substituted mono-substituted amino or an optionally substituted disubstituted amino. In some embodiments, when $B^1$ is a substituted pyrimidinyl, $B^1$ cannot be substituted by an amino. In some embodiments, $A^1$ cannot be bonded to $B^1$ through an N of $B^1$. In some embodiments, when $B^1$ is an optionally substituted phenyl, $R^{2A}$ cannot be a $C_{8-30}$ alkenyl. In some embodiments, $R^{2A}$ cannot be —(CH$_2$)$_3$CH=CHCH$_2$CH=CHCH$_2$CH=CHCH$_2$CH=CH(CH$_2$)$_4$CH$_3$ (for example, when $B^1$ is an optionally substituted phenyl). In some embodiments, when $B^1$ is a substituted phenyl, $B^1$ cannot be substituted by a hydroxy and an optionally substituted $C_{1-4}$ alkoxy. In some embodiments, when $B^1$ is a substituted 6-membered monocyclic heteroaryl, $B^1$ cannot be substituted by a halo. In some embodiments, when $B^1$ is a substituted 6-membered monocyclic heteroaryl, $B^1$ cannot be substituted by an optionally substituted $C_{1-8}$ alkyl. In some embodiments, when $B^1$ is an optionally substituted 6-membered monocyclic heteroaryl, $R^{2A}$ cannot be an alkyl substituted with an aryl (for example, phenyl). In some embodiments, when $B^1$ is a substituted phenyl, $B^1$ cannot be substituted by an optionally substituted O-aryl or an optionally substituted O-heteroaryl.

In some embodiments, when m is 0, then $R^2$ is H. In some embodiments, when m is 0, $R^1$ and $R^2$ are each H, then $B^1$ cannot be substituted with methyl. In some embodiments, when m is 0 and $R^1$ is H, then $R^2$ cannot be H. In some embodiments, when m is 1, $A^1$ is CH$_2$, and $R^2$ is hydrogen, then $R^1$ cannot be hydrogen.

In some embodiments, $B^1$ can be a 5-membered monocyclic heteroaryl (such as a thiazolyl, pyrazolyl, oxazolyl, thiadiazolyl or oxadiazolyl), m can be 0 or 1, and $B^1$ can be substituted by at least one substituent selected from halo, $C_{1-6}$ haloalkyl and $C_{1-8}$ alkyl. In some embodiments, when $B^1$ is a 5-membered monocyclic heteroaryl, then both $R^1$ and $R^2$ are H. In some embodiments, when $B^1$ is a 5-membered monocyclic heteroaryl, then both $R^1$ and $R^2$ are H, and $B^1$ is substituted by at least one substituent selected from halo, $C_{1-6}$ haloalkyl and $C_{1-8}$ alkyl. In some embodiments, when $B^1$ is a 5-membered monocyclic heteroaryl, then m is 0. In some embodiments, when $B^1$ is a 5-membered monocyclic heteroaryl, then m is 1. In some embodiments, when $B^1$ is a 5-membered monocyclic heteroaryl, then $B^1$ is substituted by at least one $C_{1-6}$ haloalkyl (such as $CF_3$ and/or $CF_2CH_3$). In some embodiments, when $B^1$ is a 5-membered monocyclic heteroaryl, then $B^1$ is substituted by at least one $C_{1-8}$ alkyl, such as methyl, ethyl, isopropyl and/or t-butyl. In some embodiments, when $B^1$ is a 5-membered monocyclic heteroaryl, then $B^1$ is substituted by at least halo group (for example, at least one fluoro and/or at least one chloro).

In some embodiments, $B^1$ cannot be a substituted or an unsubstituted furanyl. In some embodiments, B cannot be a substituted or an unsubstituted furazanyl. In some embodiments, $B^1$ cannot be a substituted or an unsubstituted thiophenyl. In some embodiments, $B^1$ cannot be a substituted or an unsubstituted pyrrole. In some embodiments, $B^1$ cannot be a substituted or an unsubstituted oxazolyl. In some embodiments, $B^1$ cannot be a substituted or an unsubstituted 1,2,3-oxadiazolyl. In some embodiments, $B^1$ cannot be a substituted or an unsubstituted 1,2,4-oxadiazolyl. In some embodiments, $B^1$ cannot be a substituted or an unsubstituted 1,3,4-oxadiazolyl. In some embodiments, $B^1$ cannot be a substituted or an unsubstituted thiazolyl. In some embodiments, $B^1$ cannot be a substituted or an unsubstituted 1,2,3-thiadiazolyl. In some embodiments, $B^1$ cannot be a substituted or an unsubstituted 1,3,4-thiadiazolyl. In some embodiments, $B^1$ cannot be a substituted or an unsubstituted 1,2,4-thiadiazolyl. In some embodiments, $B^1$ cannot be a substituted or an unsubstituted imidazolyl. In some embodiments, $B^1$ cannot be a substituted or an unsubstituted pyrazolyl. In some embodiments, $B^1$ cannot be a substituted or an unsubstituted isoxazolyl. In some embodiments, $B^1$ cannot be a substituted or an unsubstituted isothiazolyl. In some embodiments, $B^1$ cannot be a substituted or an unsubstituted triazolyl. In some embodiments, $B^1$ cannot be a substituted or an unsubstituted tetrazolyl.

In some embodiments, $B^1$ can be a 6-membered monocyclic heteroaryl (such as pyridinyl, pyrimidinyl, pyrazinyl or pyridizinyl), m can be 0 or 1, and $B^1$ can be substituted by at least one substituent selected from halo, $C_{1-6}$ haloalkyl and $C_{1-8}$ alkyl. In some embodiments, when $B^1$ is a 6-membered monocyclic heteroaryl, then both $R^1$ and $R^2$ are H. In some embodiments, when $B^1$ is a 6-membered monocyclic heteroaryl, then both $R^1$ and $R^2$ are H, and $B^1$ is substituted by at least one substituent selected from halo, $C_{1-6}$ haloalkyl and $C_{1-8}$ alkyl. In some embodiments, when $B^1$ is a 6-membered monocyclic heteroaryl, then m is 0. In some embodiments, when $B^1$ is a 6-membered monocyclic heteroaryl, then m is 1. In some embodiments, when $B^1$ is a 6-membered monocyclic heteroaryl, then $B^1$ is substituted by at least one $C_{1-6}$ haloalkyl (such as $CF_3$ and/or $CF_2CH_3$). In some embodiments, when $B^1$ is a 6-membered monocyclic heteroaryl, then $B^1$ is substituted by at least one $C_{1-8}$ alkyl, such as methyl, ethyl, isopropyl and/or t-butyl. In some embodiments, when $B^1$ is a 6-membered monocyclic heteroaryl, then $B^1$ is substituted by at least halo group (for example, at least one fluoro and/or at least one chloro).

In some embodiments, $B^1$ cannot be a substituted or an unsubstituted pyridinyl. In some embodiments, $B^1$ cannot be a substituted or an unsubstituted pyrimidinyl. In some embodiments, $B^1$ cannot be a pyrazinyl. In some embodiments, $B^1$ cannot be a substituted or an unsubstituted pyridazinyl. In some embodiments, $B^1$ cannot be a substituted or an unsubstituted 1,2,3-triazinyl. In some embodiments, $B^1$ cannot be a 1,2,4-triazinyl. In some embodiments, $B^1$ cannot be a substituted or an unsubstituted 1,2,4,5-tetrazinyl. In some embodiments, $B^1$ cannot be a 1,2,3,4-tetrazinyl.

In some embodiments, when $B^1$ is a phenyl, m is 0 or 1, and $B^1$ is substituted by at least one substituent selected from halo, $C_{1-6}$ haloalkyl and $C_{1-8}$ alkyl. In some embodiments, when $B^1$ is a phenyl, m is 0 or 1, and $B^1$ is substituted in the para-position by at least one substituent selected from halo, $C_{1-6}$ haloalkyl and $C_{1-8}$ alkyl. In some embodiments, when $B^1$ is a phenyl, m is 0, and $B^1$ is substituted in the para-position by at least one substituent selected from halo, $C_{1-6}$ haloalkyl and $C_{1-8}$ alkyl. In some embodiments, when $B^1$ is a phenyl, then both $R^1$ and $R^2$ are H. In some embodiments, when $B^1$ is a phenyl, m is 0, both $R^1$ and $R^2$ are H, and $B^1$ is substituted in the para-position by at least one substituent selected from halo, $C_{1-6}$ haloalkyl and $C_{1-8}$ alkyl. In some embodiments, when $B^1$ is a phenyl, m is 0 or 1, both $R^1$ and $R^2$ are H, and $B^1$ is substituted in the para-position by at least one substituent selected from halo, $C_{1-6}$ haloalkyl and $C_{1-8}$ alkyl. In some embodiments, when $B^1$ is phenyl, then both $R^1$ and $R^2$ are H, and $B^1$ is substituted by at least one substituent selected from halo, $C_{1-6}$ haloalkyl and $C_{1-8}$ alkyl. In some embodiments, when $B^1$ is phenyl, then m is 0. In some embodiments, when $B^1$ is a phenyl, then m is 1. In some embodiments, when $B^1$ is phenyl, then $B^1$ is substituted by at least one $C_{1-6}$ haloalkyl (such as $CF_3$ and/or $CF_2CH_3$). In some embodiments, when $B^1$ is phenyl, then $B^1$ is substituted by at least one $C_{1-8}$ alkyl, such as methyl, ethyl, isopropyl and/or t-butyl. In some embodiments, when $B^1$ is phenyl, then $B^1$ is substituted by at least halo group (for example, at least one fluoro and/or at least one chloro). In some embodiments, when $B^1$ is phenyl, then $R^2$ is not H. In some embodiments, when $B^1$ is phenyl, then $R^{2A}$ is methyl.

In some embodiments, $B^1$ cannot be a mono-substituted phenyl. In some embodiments, $B^1$ cannot be a di-substituted phenyl. In some embodiments, $B^1$ cannot be a tri-substituted phenyl. In some embodiments, $B^1$ cannot be a para-substituted phenyl. In some embodiments, $B^1$ cannot be an ortho-substituted phenyl. In some embodiments, $B^1$ cannot be a meta-substituted phenyl.

In some embodiments, $B^1$ cannot include phenyl having a para-OH or —NH— substitution. In some embodiments, $B^1$ cannot include phenyl substituted with a para-hydroxy. In still other embodiments, when m is 0, then $B^1$ cannot include phenyl substituted with a hydroxy (such as a para-hydroxy). In other embodiments, when $B^1$ includes phenyl substituted by a para-hydroxy, then m is 1.

In some embodiments, $B^1$ cannot be substituted with halogen. In some embodiments, $B^1$ cannot be substituted with hydroxy. In some embodiments, $B^1$ cannot be substituted with an optionally substituted $C_{1-4}$ alkoxy. In some embodiments, $B^1$ cannot be substituted with an optionally substituted $C_{1-8}$ alkyl. In some embodiments, $B^1$ cannot be substituted with an optionally substituted $C_{3-20}$ cycloalkyl. In some embodiments, $B^1$ cannot be substituted with an optionally substituted aryl (such as an optionally substituted phenyl). In some embodiments, $B^1$ cannot be substituted with an optionally substituted heteroaryl. In some embodiments, $B^1$ cannot be substituted with an optionally substituted heterocyclyl. In some embodiments, $B^1$ cannot be substituted with an optionally substituted $C_{1-6}$ haloalkyl. In some embodiments, $B^1$ cannot be substituted with cyano. In some embodiments, $B^1$ cannot be substituted with an optionally substituted $C_{2-8}$ alkenyl. In some embodiments, $B^1$ cannot be substituted with an optionally substituted $C_{2-8}$ alkynyl. In some embodiments, $B^1$ cannot be substituted with an optionally substituted $C_{3-20}$ cycloalkenyl. In some embodiments, $B^1$ cannot be substituted with an optionally substituted aryl(alkyl). In some embodiments, $B^1$ cannot be substituted with an optionally substituted heteroaryl(alkyl). In some embodiments, $B^1$ cannot be substituted with an optionally substituted heterocyclyl(alkyl). In some embodiments, $B^1$ cannot be substituted with an optionally substituted acyl. In some embodiments, $B^1$ cannot be substituted with an optionally substituted thiocarbonyl. In some embodiments, $B^1$ cannot be substituted with an optionally substituted O-carbamyl. In some embodiments, $B^1$ cannot be substituted with an optionally substituted N-carbamyl. In some embodiments, $B^1$ cannot be substituted with an optionally substituted O-thiocarbamyl. In some embodiments, $B^1$ cannot be substituted with an optionally substituted N-thiocarbamyl. In some embodiments, $B^1$ cannot be substituted with an optionally substituted C-amido. In some embodiments, $B^1$ cannot be substituted with an optionally substituted N-amido. In some embodiments, $B^1$ cannot be substituted with an optionally substituted C-thioamido. In some embodiments, $B^1$ cannot be substituted with an optionally substituted N-thioamido. In some embodiments, $B^1$ cannot be substituted with an optionally substituted S-sulfonamido. In some embodiments, $B^1$ cannot be substituted with an optionally substituted N-sulfonamido. In some embodiments, $B^1$ cannot be substituted with an optionally substituted C-carboxy. In some embodiments, $B^1$ cannot be substituted with an optionally substituted O-carboxy. In some embodiments, $B^1$ cannot be substituted with an optionally substituted sulfenyl. In some embodiments, $B^1$ cannot be substituted with an optionally substituted sulfinyl. In some embodiments, $B^1$ cannot be substituted with an optionally substituted sulfonyl. In some embodiments, $B^1$ cannot be substituted with an optionally substituted haloalkoxy. In some embodiments, $B^1$ cannot be substituted with an amino. In some embodiments, $B^1$ cannot be substituted with a mono-substituted amino group. In some embodiments, $B^1$ cannot be substituted with a di-substituted amino group.

In some embodiments, $B^1$ cannot be substituted with a methyl. In other embodiments, $B^1$ cannot be substituted with an ethyl. In other embodiments, $B^1$ cannot be substituted with an allyl. In other embodiments, $B^1$ cannot be substituted with a vinyl. In other embodiments, $B^1$ cannot be substituted with a propargyl. In other embodiments, $B^1$ cannot be substituted with an isoprenyl.

In some embodiments, $B^1$ cannot be substituted with monocyclic cycloalkyl. In other embodiments, $B^1$ cannot be substituted with a cyclopropyl. In some embodiments, $B^1$ cannot be substituted with a substituted or unsubstituted cyclohexyl. In some embodiments, $B^1$ cannot be substituted with a substituted or unsubstituted cyclopentyl. In some embodiments, $B^1$ cannot be substituted with a multicyclic cycloalkyl. In some embodiments, $B^1$ cannot be substituted with a substituted or an unsubstituted norbornyl. In some embodiments, $B^1$ cannot be substituted with a substituted or an unsubstituted adamantyl.

In some embodiments, $B^1$ cannot be substituted with an aryl. In other embodiments, $B^1$ cannot be substituted with an unsubstituted phenyl. In other embodiments, $B^1$ cannot be substituted with a substituted phenyl. In some embodiments, $B^1$ cannot be substituted with a mono-substituted phenyl. In some embodiments, $B^1$ cannot be substituted with a para-substituted phenyl. In some embodiments, $B^1$ cannot be substituted with a meta-substituted phenyl. In some embodiments, $B^1$ cannot be substituted with an ortho-substituted phenyl. In some embodiments, $B^1$ cannot be substituted with a tri-substituted phenyl. In some embodiments, $B^1$ cannot be substituted with a substituted or an unsubstituted naphthyl.

In some embodiments, $B^1$ cannot be substituted with a substituted or an unsubstituted heteroaryl. In other embodiments, $B^1$ cannot be substituted with a substituted or an unsubstituted pyridinyl.

In some embodiments, $B^1$ cannot be substituted with a substituted or an unsubstituted heterocyclyl. In other embodiments, $B^1$ cannot be substituted with a substituted or an unsubstituted piperidinyl. In other embodiments, $B^1$ cannot be substituted with a substituted or an unsubstituted morpholinyl.

In some embodiments, $B^1$ cannot be substituted with a substituted or an unsubstituted aryl($C_{1-6}$ alkyl). In some embodiments, $B^1$ cannot be substituted with a substituted or an unsubstituted benzyl.

In some embodiments, $B^1$ cannot be substituted with a substituted or an unsubstituted $C_{1-8}$ haloalkyl. In other embodiments, $B^1$ cannot be substituted with an unsubstituted $C_{1-8}$ haloalkyl. In some embodiments, $B^1$ cannot be substituted with $CF_3$. In some embodiments, $B^1$ cannot be substituted with $CHF_2$. In some embodiments, $B^1$ cannot be substituted with $CH_2F$. In some embodiments, $B^1$ cannot be substituted with $CH_2CF_3$. In some embodiments, $B^1$ cannot be substituted with $CF_2CH_3$.

In some embodiments, $B^1$ cannot be substituted with a sulfonyl. In some embodiments, $B^1$ cannot be substituted with $SO_2R^{++}$, wherein $R^{++}$ can be an optionally substituted $C_{1-6}$ alkyl an optionally substituted phenyl, or an optionally substituted $C_{1-6}$ haloalkyl.

In some embodiments, $R^1$ cannot be H. In other embodiments, $R^1$ cannot be D. In still other embodiments, $R^1$ cannot be a substituted $C_{1-6}$ alkyl. In yet still other embodiments, $R^1$ cannot be an unsubstituted $C_{1-6}$ alkyl. In some embodiments, $R^1$ cannot be a substituted $C_{1-6}$ haloalkyl. In other embodiments, $R^1$ cannot be an unsubstituted $C_{1-6}$ haloalkyl.

In some embodiments, $R^2$ cannot be H. In some embodiments, $NR^1R^2$ cannot be an amino group directly attached to $B^1$. In other embodiments, $NR^1R^2$ cannot be an amino group attached to $B^1$ through an optionally substituted methylene. In some embodiments, $NR^1R^2$ cannot be a mono-substituted group directly attached to $B^1$. In other embodiments, $NR^1R^2$ cannot be a mono-substituted group attached to $B^1$ through an optionally substituted methylene.

In some embodiments, $R^2$ cannot be $C(=O)R^{2A}$. In some embodiments, $NR^1R^2$ cannot be an amido group directly attached to $B^1$. In other embodiments, $NR^1R^2$ cannot be an amido group attached to $B^1$ through an optionally substituted methylene.

In some embodiments, $R^{2A}$ cannot be H. In other embodiments, $R^{2A}$ cannot be D. In still other embodiments, $R^{2A}$ cannot be a substituted $C_{1-30}$ alkyl. In yet still other embodiments, $R^{2A}$ cannot be an unsubstituted $C_{1-30}$ alkyl. In some embodiments, $R^{2A}$ cannot be substituted methyl. In some embodiments, $R^{2A}$ cannot be unsubstituted methyl. In some embodiments, $R^{2A}$ cannot be substituted ethyl. In some embodiments, $R^{2A}$ cannot be unsubstituted ethyl.

In some embodiments, $R^{2A}$ cannot be a substituted $C_{2-30}$ alkenyl. In other embodiments, $R^{2A}$ cannot be an unsubstituted $C_{2-30}$ alkenyl. In still other embodiments, $R^{2A}$ cannot be a substituted $C_{2-30}$ alkynyl. In yet still other embodiments, $R^{2A}$ cannot be an unsubstituted $C_{2-30}$ alkynyl.

In some embodiments, $R^{2A}$ cannot be a substituted $C_{3-30}$ cycloalkyl. In other embodiments, $R^{2A}$ cannot be an unsubstituted $C_{3-30}$ cycloalkyl. In some embodiments, $R^{2A}$ cannot be a mono-cyclic cycloalkyl. In other embodiments, $R^{2A}$ cannot be a bi-cyclic or tri-cyclic cycloalkyl (such as a fused, bridged and/or spiro cycloalkyl).

In some embodiments, $R^{2A}$ cannot be a substituted $C_{1-8}$ haloalkyl. In other embodiments, $R^{2A}$ cannot be an unsubstituted $C_{1-8}$ haloalkyl. In some embodiments, $R^{2A}$ cannot be one or more of the following $CF_3$, $CHF_2$, $CH_2F$, $CH_2CF_3$, $CH_2CHF_2$ and $CH_2CH_2F$.

In some embodiments, $R^{2A}$ cannot be a substituted $C_{1-4}$ alkoxy. In other embodiments, $R^{2A}$ cannot be an unsubstituted $C_{1-4}$ alkoxy. In some embodiments, $R^{2A}$ cannot be methoxy, ethoxy, n-propoxy, isopropoxy, n-butoxy, isobutoxy and/or tert-butoxy.

In some embodiments, m cannot be 0. In other embodiments, m cannot be 1. In some embodiments, $R^4$ cannot be H. In other embodiments, $R^4$ cannot be D. In still other embodiments, $R^4$ cannot be an unsubstituted $C_{1-8}$ alkyl. In yet still other embodiments, $R^4$ cannot be an unsubstituted $C_{1-6}$ haloalkyl, such as $CF_3$, $CHF_2$ or $CH_2F$. In some embodiments, $R^4$ cannot be unsubstituted methyl. In some embodiments, $R^4$ cannot be unsubstituted ethyl. In some embodiments, $R^5$ cannot be H. In other embodiments, $R^5$ cannot be D. In still other embodiments, $R^5$ cannot be an unsubstituted $C_{1-8}$ alkyl. In yet still other embodiments, $R^5$ cannot be an unsubstituted $C_{1-6}$ haloalkyl, such as $CF_3$, $CHF_2$ or $CH_2F$. In some embodiments, $R^5$ cannot be unsubstituted methyl. In some embodiments, $R^5$ cannot be unsubstituted ethyl. In some embodiments, $R^4$ and $R^5$ cannot be taken together to form an optionally substituted $C_{3-6}$ cycloalkyl.

Methods

The various compounds contemplated herein can be obtained from a commercial source and/or synthesized from known starting materials by various routes known to those skilled in the art. Some suitable routes are illustrated in the Examples and following references: Xiang et al., Bioorganic and Medicinal Chemistry Letters (2005) 15:2865-2869; U.S. Patent Publication No. 2883391 (filed 25 Jun. 1957); Hilfiker et al., *Bioorganic and Medicinal Chemistry Letters* (2009) 19:4292-4295; Alegaon et al., *Bioorganic and Medicinal Chemistry Letters* (2012) 22:1917-1921; Niu et al., *Journal of Organic Chemistry* (2015) 80:1018-1024; WO 2008/100622 (filed 15 Feb. 2008); Li et al., *Journal of Medicinal Chemistry* (2016) 59:8293-8305; WO 2008/002959 (filed 27 Jun. 2007); WO 2005/009941 (filed 23 Jun. 2004); Wolf et al., *Chemische Berichte* (1962) 95:2419-2423; WO 2009/139834 (filed 8 May 2009); U.S. Patent Publication No. 2005/0288308 (filed 27 Jun. 2005); Cameron et al., *Organic Process Research and Development* (2006) 10:398-402; U.S. Pat. No. 5,854,234 (filed 20 Oct. 1994); Kino et al., *Journal of Fluorine Chemistry* (2010) 131:98-105; U.S. Patent Publication No. 2007/0155738 (filed 20 Nov. 2006); Kurouchi et al., *Chemistry—A European Journal* (2014) 20:8682-8690; Froyen et al., *Tetrahedron Letters* (1997) 38:5359-5362; WO 2004/000294 (filed 17 Jun. 2003); Reuter et al., *European Journal of Organic Chemistry* (2009) 5647-5652; WO 2008/111604 (filed 12 Mar. 2008); WO 2003/093250 (filed 28 Apr. 2003); Bramley et al., *Journal of the Chemical Society, Perkin Transactions 1* (1987) 639-643; WO 2004/072066 (filed 10 Feb. 2004); WO 2007/140439 (filed 31 May 2007); WO 2000/021943 (filed 12 Oct. 1999); WO 2008/010921 (filed 6 Jul. 2007). Salts can be formed using methods known to those skilled in the art and described herein, for example, reacting an amine with a suitable acid (such as HCl).

Pharmaceutical Compositions

Some embodiments described herein relate to a pharmaceutical composition, that can include an effective amount of one or more compounds described herein (e.g., a compound of Formula (I), or a pharmaceutically acceptable salt thereof) and a pharmaceutically acceptable carrier, diluent, excipient or combination thereof.

The term "pharmaceutical composition" refers to a mixture of one or more compounds disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, and salicylic acid. Pharmaceutical compositions will generally be tailored to the specific intended route of administration.

The term "physiologically acceptable" defines a carrier, diluent or excipient that does not abrogate the biological activity and properties of the compound nor cause appreciable damage or injury to an animal to which delivery of the composition is intended.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks appreciable pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the pH and isotonicity of human blood.

As used herein, an "excipient" refers to an essentially inert substance that is added to a pharmaceutical composition to provide, without limitation, bulk, consistency, stability, binding ability, lubrication, disintegrating ability etc., to the composition. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound exist in the art including, but not limited to, oral, rectal, pulmonary, topical, aerosol, injection, infusion and parenteral delivery, including intramuscular, subcutaneous, intravenous, intramedullary injections, intrathecal, direct intraventricular, intraperitoneal, intranasal and intraocular injections.

One may also administer the compound in a local rather than systemic manner, for example, via injection or implantation of the compound directly into the affected area, often in a depot or sustained release formulation. Furthermore, one may administer the compound in a targeted drug delivery system, for example, in a liposome coated with a tissue-specific antibody. The liposomes will be targeted to and taken up selectively by the organ. For example, intranasal or pulmonary delivery to target a respiratory infection may be desirable.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

Methods of Use

Some embodiments provided herein relate to a method of treating a disease or condition that can include administering to a subject an effective amount of a compound of Formula (I), or a pharmaceutically acceptable salt thereof. Other embodiments provided herein relate to a method of treating a disease or condition that can include contacting a cell in the central and/or peripheral nervous system of a subject with an effective amount of a compound of Formula (I), or a pharmaceutically acceptable salt thereof. In some embodiments, the subject can be at risk of developing a disease or condition that is responsive to acetaminophen and/or a NSAID. In some embodiments, the disease or condition can be one or more of the following: pain, fever, inflammation, ischemic injury (such as myocardial and/or cerebral) and/or neuronal injury. In some embodiments, the subject can be post-operative and has, or is believed to have or has actually developed post-operative pain. In some embodiments, the subject can be in need of treatment for acute pain and has, is believed to have or has actually developed acute pain. In some embodiments, the subject can be in need of treatment for chronic pain and has, is believed to have or has actually developed chronic pain. In some embodiments, the subject can be in need of treatment for neuropathic pain and has, is believed to have or has actually developed neuropathic pain. The basis for determining the need for treatment can be based on an underlying condition or conditions, from indication by the subject or on other bases known to practitioners. In some embodiments, a compound of Formula (I), or a pharmaceutically acceptable salt thereof, can be provided (such as administered) prophylactically, for example, prophylactically for pain (such as post-operative pain).

In some embodiments, a compound of Formula (I), or a pharmaceutically acceptable salt thereof, can contact a cell in the central nervous system, for example, the brain and/or spinal cord. In some embodiments, a compound of Formula (I), or a pharmaceutically acceptable salt thereof, can contact a cell in the peripheral nervous system, for example, the ganglia and/or nervous system outside the brain and spinal cord.

In some embodiments, a compound of Formula (I), or a pharmaceutically acceptable salt thereof, can contact a TRP (transient receptor potential) channels modulator (such as TRPV1 and/or TRPA1), and thereby treat a disease or condition described herein. In some embodiments, a compound of Formula (I), or a pharmaceutically acceptable salt thereof, can contact a cannabinoid receptors modulator (such as CB1 and/or CB2), and thereby treat a disease or condition described herein. In some embodiments, a compound of Formula (I), or a pharmaceutically acceptable salt thereof, can contact a serotonin receptor (for example, 5HT1, 5HT2, 5HT3, 5HT4, 5HT5, 5HT6 and/or 5HT7) and modulate its activity, and thereby treat a disease or condition described herein. In some embodiments, a compound of Formula (I), or a pharmaceutically acceptable salt thereof, can act as an anandamide reuptake inhibitor, and thereby treat a disease or condition described herein. In some embodiments, a compound of Formula (I), or a pharmaceutically acceptable salt thereof, can be a substrate for the fatty acid amide hydrolase (FAAH), and thereby treat a disease or condition described herein.

Some embodiments generally relate to a method of treating pain of any etiology, including acute pain, chronic pain and neuropathic pain, and any pain in which acetaminophen is prescribed. Examples of pain include post-surgical pain; post-operative pain (including dental pain); migraine; headache and trigeminal neuralgia; pain associated with burn, wound and/or kidney stone; pain associated with trauma (including traumatic head injury); neuropathic pain (e.g., central and peripheral pain); pain associated with musculoskeletal disorders; strains; sprains; contusions; fractures; myalgia; nociceptive pain (for example, rheumatoid arthritis and osteoarthritis pain); cystitis; visceral pain (such as, pancreatitis, inflammatory bowel disease and internal organ pain); ankylosing spondylitis; sero-negative (non-rheumatoid) arthropathies; non-articular rheumatism and peri-articular disorders; and mixed pain. Central pain includes post-stroke pain, pain associated with multiple sclerosis, spinal cord injury, migraine and HIV-related neuropathic pain. Peripheral pain includes post-herpetic neuralgia and diabetic neuropathy. Mixed pain includes pain associated with cancer (including "break-through pain" and pain associated with terminal cancer), lower back and fibromyalgia. Examples of pain with an inflammatory component (in addition to some of those described above) include rheumatic pain, pain associated with mucositis and pain associated with dysmenorrhea. In some embodiments, a method and/or a composition described herein can be used for treating or preventing post-surgical pain. In some embodiments, a method and/or a composition described herein can be used for treating or preventing of cancer pain. In some embodiments, a method and/or a composition described herein can be used for treating or preventing of osteoarthritis and/or rheumatoid arthritis pain. In some embodiments, a method and/or a composition described herein can be used for treating or preventing of migraine pain. In some embodiments, a method and/or a composition described herein can be used for treating or preventing of lower back pain and/or fibromyalgia pain. In some embodiments, a method and/or a composition described herein can be used for treating or preventing pain that is selected from pain associated with surgery, trauma, osteoarthritis, rheumatoid arthritis, lower back pain, fibromyalgia, postherpetic neuralgia, diabetic neuropathy, HIV-associated neuropathy and complex regional pain syndrome. Additionally information regarding pain is provided in Melnikova, I., "Pain market" (2010) 9(8):589-590, which is hereby incorporated by reference in its entirety.

In some embodiments, a compound of Formula (I), or a pharmaceutically acceptable salt thereof, can be used for treating or preventing pain and/or a fever (e.g., in adults, children and/or infants, and in animal health to treat animals such as the cat, dog or horse). Compounds of Formula (I), or pharmaceutically acceptable salts thereof, can be used to treat a variety and varying degrees of pain. In some embodiments, the pain can be acute pain (e.g., acute pain following surgery, such as orthopedic surgery of adults, children, and/or infants). In some embodiments, the pain can be chronic pain (e.g., pain lasting days, weeks, months, or years, and optionally following an initial event, such as an injury, trauma, surgery, or onset of disease).

In some embodiments, a compound of Formula (I), or a pharmaceutically acceptable salt thereof, can be used for treating and/or preventing a fever, such as endotoxin-induced fever (e.g., endotoxin-induced fever in adults, children, and/or infants). In some embodiments, the fever can be selected from low-grade fever, moderate fever, high-grade fever and hyperpyrexia fever. In some embodiments, the fever can be selected from Pel-Ebstein fever, continuous fever, intermittent fever and remittent fever.

As described herein, compounds of Formula (I), or pharmaceutically acceptable salts thereof, can be used in a various subjects. In some embodiments, the subject can be a child and/or an infant, for example, a child or infant with a fever. In other embodiments, the subject can be an adult. In other embodiments, the subject can be an animal such as a cat, dog or horse. As described herein, compounds of Formula (I), or pharmaceutically acceptable salts thereof, can be administered by a physicians or a veterinarian as appropriate.

Some embodiments described herein relate to a method of delaying the onset of analgesia in a subject in need thereof, wherein the method can include administering to the subject an effective amount of Formula (I) that delays drug action by greater than about 5 minutes, or 10 minutes, or 15 minutes, or 30 minutes, or 1 hour, or 2, hours, or 3 hours, or 4 hours, or 6 hours, or 8 hours, or 10 hours, or 12 hours, or 18 hours, or 24 hours. Other embodiments described herein relate to a method of delaying the onset of analgesia in a subject in need thereof, wherein the method can include contacting a cell in the central and/or peripheral nervous system of a subject with an effective amount of Formula (I) that delays drug action by greater than about 5 minutes, or 10 minutes, or 15 minutes, or 30 minutes, or 1 hour, or 2, hours, or 3 hours, or 4 hours, or 6 hours, or 8 hours, or 10 hours, or 12 hours, or 18 hours, or 24 hours.

In some embodiments, a compound of Formula (I), or a pharmaceutically acceptable salt thereof, may provide greater reduction or prevention of pain than acetaminophen in the early/acute phase (0-10 minutes). In some embodiments, a compound of Formula (I), or a pharmaceutically acceptable salt thereof, may provide greater reduction or prevention of pain than acetaminophen in the late/tonic phase (10-35 minutes).

As described herein, compounds of Formula (I), or a pharmaceutically acceptable salt thereof, can be administered by a variety of methods. In any of the methods described herein, administration can be by injection, infusion and/or intravenous administration over the course of 1 minute, 5 minutes, 10 minutes, 30 minutes, 1 hour, 2 hours, 6 hours, 12 hours, 24 hours or longer, or any intermediate time. Such administration can, in some circumstances, substitute for or significantly reduce the need for administration of an opiate. Some methods described herein can include intravenous administration to a subject in need thereof, for example, to a subject to manage post-operative or other acute or chronic pain, in either a bolus dose or by infusion over minutes, hours, or days. Other methods described herein can include oral, intravenous, subcutaneous and/or intraperitoneal administration to a subject in need thereof, for example, to a subject to manage post-operative or other acute pain or chronic pain.

Other embodiments described herein relate to a method for selecting a therapy for managing or treating pain in a subject in need thereof, that can include evaluating whether the subject is at risk for hepatic toxicity from pain therapy, and selecting therapy that includes a compound of Formula (I), or a pharmaceutically acceptable salt thereof, to reduce or eliminate such risk. The method can further include providing the selected therapy that includes a compound of Formula (I), or a pharmaceutically acceptable salt thereof, to the subject. In some embodiments, a compound of Formula (I), or a pharmaceutically acceptable salt thereof, can be of significant benefit in pain management in hospitals or other care facilities (for example, a nursing home).

As used herein, the terms "prevent" and "preventing," mean a subject does not experience and/or develop pain and/or fever, or the severity of the pain and/or fever is less compared to the severity of the pain and/or fever if the subject has not been administered/received the compound. Examples of forms of prevention include prophylactic administration to a subject who is going to undergo surgery.

As used herein, the terms "treat," "treating," "treatment," "therapeutic," and "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the subject's overall feeling of well-being or appearance.

The terms "therapeutically effective amount" and "effective amount" are used to indicate an amount of an active compound, or pharmaceutical agent, that elicits the biological or medicinal response indicated. For example, a therapeutically effective amount of compound can be the amount needed to prevent, alleviate or ameliorate symptoms of disease or prolong the survival of the subject being treated This response may occur in a tissue, system, animal or human and includes alleviation of the signs or symptoms of the disease being treated. Determination of an effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician. In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or conditions.

In general, however, a suitable dose will often be in the range of from about 0.15 mg/kg to about 100 mg/kg. For example, a suitable dose may be in the range from about 1 mg/kg to about 75 mg/kg of body weight per day, such as about 0.75 mg/kg to about 50 mg/kg of body weight of the recipient per day, about 1 mg/kg to 90 mg/kg of body weight of the recipient per day, or about 10 mg/kg to about 60 mg/kg of body weight of the recipient per day.

The compound may be administered in unit dosage form; for example, containing 1 to 2000 mg, 10 to 1000 mg or 5 to 500 mg of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials, in vivo studies and in vitro studies. For example, useful dosages of compounds of Formula (I), or pharmaceutically acceptable salts thereof, can be determined by comparing their in vitro activity, and in vivo activity in animal models. Such comparison can be done against an established analgesic drug, such as acetaminophen.

Dosage amount and interval may be adjusted individually to provide plasma levels of the active moiety which are sufficient to maintain the modulating effects, or minimal effective concentration (MEC). The MEC will vary for each compound but can be estimated from in vivo and/or in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug cannot be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in animal health and veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, dogs or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

Combination Drugs

One or more compounds of Formula (I), or a pharmaceutically acceptable salt thereof, can be provided alone or in combination with another drug(s). In some embodiments, the other drug(s) can be an opioid analgesic. Any of the known opioid analgesics can be combined with a compound of Formula (I), or a pharmaceutically acceptable salt thereof. As non-limiting examples, such opioid analgesics include morphine, codeine, hydrocodone, oxycodone, fentanyl, pethidine, methadone, pentazocine, sufentanil, levorphanol, dihydrocodeine, nalbuphine, butorphanol, tramadol, meptazinol, buprenorphine, dipipanone, alfentanil, remifentanil, oxymorphone, tapentadol, propoxyphene and hydromorphone.

In some embodiments, a compound of Formula (I), or a pharmaceutically acceptable salt thereof, can be provided in a dosage form (for example, an oral dosage form, an intravenous dosage form and/or an intraperitoneal dosage form), in combination with one of the following exemplary opioids: 1-20 mg hydrocodone (such as hydrocodone bitartrate), preferably 2.5 mg, 5 mg, 7.5 mg or 10 mg of hydrocodone or salt thereof; or 1-20 mg oxycodone, preferably 2.5 mg, 5 mg, 7.5 mg or 10 mg of hydrocodone or salt thereof (such as the hydrochloride salt). In some embodiments, the amount of a compound of Formula (I), or a pharmaceutically acceptable salt thereof, can be in the range of about 20 to about 2000 mg.

In some embodiments, a compound of Formula (I) can be combined with one or more non-steroidal anti-inflammatory drugs (NSAIDs). As non-limiting examples, such NSAIDs include celecoxib, ketorolac, ketoprofen, indomethacin, sulindac, etodolac, mefenamic acid, meclofenamic acid, meclofenamate sodium, flufenamic acid, tolmetin, diclofenac, diclofenac sodium, ibuprofen, naproxen, naproxen sodium, fenoprofen, flurbiprofen, oxaprozin, piroxicam, meloxicam, ampiroxicam, droxicam, lornoxicam, cinnoxicam, sudoxicam, and tenoxicam, and pharmaceutically acceptable salts of the foregoing. In some embodiments, an NSAID can be a COX-2 inhibitor.

In some embodiments, a compound of Formula (I), or a pharmaceutically acceptable salt thereof, can be provided in a dosage form (for example, an oral dosage form, an intravenous dosage form and/or an intraperitoneal dosage form), in combination with one of the following exemplary NSAIDs: 10-1000 mg ibuprofen, for example 100 mg, 250 mg, 500 mg or 750 mg of ibuprofen or salt thereof; 100-1000 mg naproxen, for example 100 mg, 250 mg, 500 mg or 750 mg of naproxen or salt thereof (such as the sodium salt); 10-500 mg ketorolac, for example 10 mg, 15 mg, 30 mg, 50 mg or 100 mg of ketorolac or salt thereof 10-500 mg ketoprofen, for example 10 mg, 75 mg, 200 mg or 500 mg of ketoprofen or salt thereof; or 10-1000 mg celecoxib, for example 100 mg, 250 mg, 500 mg or 750 mg of celecoxib or salt thereof. In some embodiments, the amount of a compound of Formula (I), or a pharmaceutically acceptable salt thereof, can be in the range of about 20 to about 2000 mg.

Other combinations include combination of a compound of Formula (I), or a pharmaceutically acceptable salt thereof, with butalbital, codeine, dihydrocodeine, and/or aspirin. The other drug(s) can be provided using routes known to those skilled in the art and/or described herein. In some embodiments, a compound of Formula (I), or a pharmaceutically acceptable salt thereof, and another drug(s) can be provided in the same dosage form. In other embodiments, a compound of Formula (I), or a pharmaceutically acceptable salt thereof, and another drug(s) can be provided in the separate dosage forms. In some embodiments, a compound of Formula (I), or a pharmaceutically acceptable salt thereof, and another drug(s) can be by the same route (for example, both intravenously) or by different routes (for example, one orally and the other intraperitoneally). In some embodiments, a compound of Formula (I), or a pharmaceutically acceptable salt thereof, can be provided before another drug(s) (such as an opiate). In other embodiments, a compound of Formula (I), or a pharmaceutically acceptable salt thereof, can be provided simultaneously with another drug(s) (such as an opiate). In still other embodiments, a compound of Formula (I), or a pharmaceutically acceptable salt thereof, can be provided after another drug(s) (such as an opiate).

In some embodiments, a combination of a compound of Formula (I), or a pharmaceutically acceptable salt thereof, and an opioid analgesic can synergistically relieve pain. In some embodiments, the synergistic relief of pain can reduce opioid use. Some embodiments disclosed herein relate to a method of managing, treating and/or reducing pain that can include administering an effective amount of a combination of a compound of Formula (I), or a pharmaceutically acceptable salt thereof, and an opioid analgesic to a subject. Some embodiments disclosed herein relate to a method for reducing opioid use in pain management, that can include administering an amount of a compound of Formula (I), or a pharmaceutically acceptable salt thereof, in combination with an amount of an opioid analgesic, wherein the amount of the opioid analgesic in the combination is less than the amount of opioid analgesic needed to achieve approximately the same level of pain management when the opioid analgesic is administered alone. Methods known for evaluating pain management is known to those skilled in the art, for example, pain assessment tools. Some embodiments disclosed herein relate to a method for decreasing the risk of opioid dependency that can include administering an amount of a compound of Formula (I), or a pharmaceutically acceptable salt thereof, in combination with an amount of an opioid analgesic, wherein the amount of the opioid analgesic in the combination is less than the amount of opioid analgesic needed to achieve approximately the same level of pain management when the opioid analgesic is administered alone. Some embodiments disclosed herein relate to a method for treating pain and/or fever along with treating opioid dependency that can include administering an amount of a compound of Formula (I), or a pharmaceutically acceptable salt thereof, in combination with an amount of an opioid analgesic.

EXAMPLES

Additional embodiments are disclosed in further detail in the following examples, which are not in any way intended to limit the scope of the claims.

Example 1

Compound 11

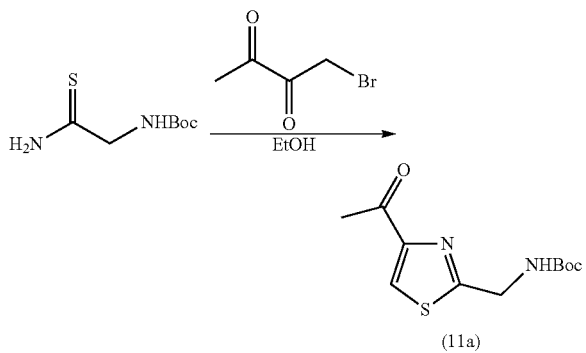

A mixture of 1-Bromo-butane-2,3-dione (1.63 g, 10 mmol) and thiocarbamoylmethyl-carbamic acid tert-butyl ester (1.90 g, 10 mmol) in EtOH (20 mL) was stirred at rt for 2 hrs until TLC shows complete conversion of starting material to a new spot. $K_2CO_3$ (1.37 g, 10 mmol) was added and the mixture was stirred for additional 30 min and the mixture was then diluted in EtOAc and washed with water. The organic layer was dried over $Na_2SO_4$ and concentrated. The residue was purified by column chromatography ($SiO_2$, Hexanes/EtOAc) to afford 11a (1.1 g, 43%) as a yellow solid $^1$H NMR (500 MHz, $CDCl_3$) δ 8.07 (s, 1H), 5.26 (s, 1H), 4.64-4.62 (d, J=10 Hz, 2H), 2.64 (s, 3H), 1.48 (s, 9H). $C_{11}H_{16}N_2O_3S$ Exact Mass: 256.09, ESI$^+$ m/z 257.2 [M+H]$^+$.

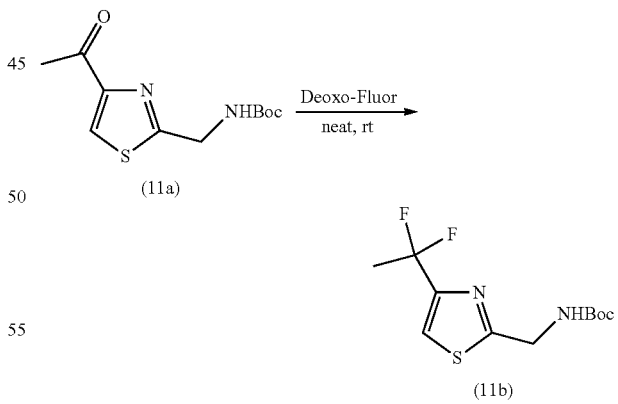

Under nitrogen, 11a (1.2 g, 4.68 mmol) was dissolved in DCM (5 mL) and DAST (3.5 mL) was added followed by one drop of anhydrous EtOH. The mixture was stirred at rt for 24 hrs. The solvent was removed by rotavap and the residue was purified by column chromatography ($SiO_2$, Hexanes/EtOAc) followed by C18 reverse phase column to afford 11b (220 mg, 16.9%) as a pale yellow solid $^1$H NMR (400 MHz, $CDCl_3$) δ 7.48 (1, 1H), 5.26 (s, 1H), 4.62-4.60

(m, 2H), 2.00 (t, J=20 Hz, 3H), 1.47 (s, 9H). $C_{11}H_{16}F_2N_2O_2S$ Exact Mass: 278.09, ESI+ m/z 279.2 [M+H]+.

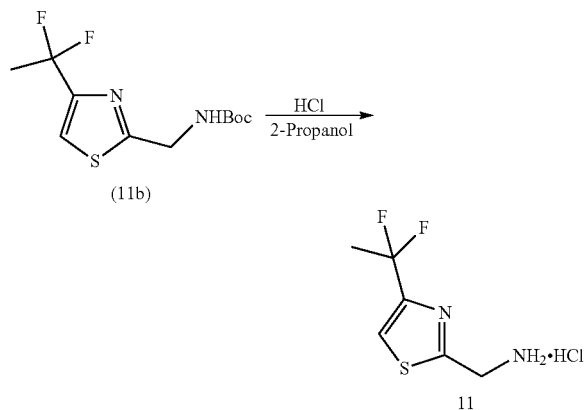

Under nitrogen, 4N HCl in dioxane (2 mL) was added to 11b (220 mg, 0.790 mmol) and the mixture was stirred for 4 hrs until no starting material left by LCMS analysis. The solvent was removed by rotavap. The residue was dried under high vacuum to afford 11 as its hydrochloride salt (150 mg, 89%) as a white solid. $^1$H NMR (400 MHz, CDCl$_3$) δ 7.96 (s, 1H), 4.55 (s, 2H), 2.04 (t, J=20 Hz, 3H). $C_6H_8F_2N_2S$ Exact Mass: 178.04. ESI+ m/z 179.1 [M+H]+.

Example 2

Compound 12

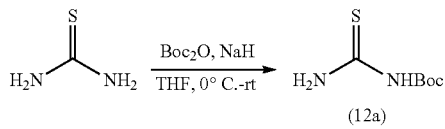

Synthesis of 12a from thiourea (3.0 g, 39.41 mmol) was carried out according to the known literature procedure (Synthetic Communications (2002), 32(11):1671-1674) to afford 12a (2.5 g, 36%) as a white solid. $^1$H NMR (500 MHz, CDCL$_3$) δ 9.21 (brs, 1H), 8.14 (brs. 1H), 7.02 (brs, 1H), 1.48 (s, 9H). LCMS (ESI, m/z) 177.3 [M+H]+.

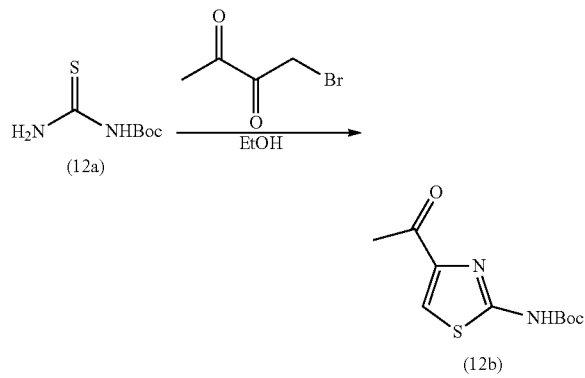

A solution of 1-bromobutane-2,3-dione (1.0 g, 6.06 mmol) and 12a (1.07 g, 6.06 mmol) in Ethanol (15 mL) was stirred at room temperature for 2 hours. Solid Na$_2$CO$_3$ (1.0 g) was added. The mixture was stirred for 40 min., filtered and evaporated. The residue was suspended in DCM (100 mL). The resulting suspension was stirred at ambient temperature for 1 hour and filtered. The filtrate was evaporated to afford 12b (1.41 g, 96%) as a brown solid which was used without further purification. $^1$H NMR (300 MHz, DMSO-d$_6$) δ 11.71 (brs, 1H), 8.05 (s, 1H), 2.47 (s, 3H), 1.47 (s, 9H). LCMS (ESI, m/z) 243.5 [M+H]+.

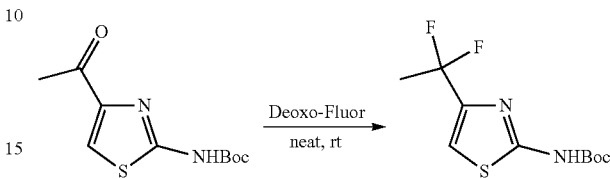

A mixture of 12b (0.3 g, 1.24 mmol) and Deoxo-Fluor (0.456 mL, 2.476 mmol) was stirred in a sealed vial at room temperature for 24 hours. The crude mixture was purified by flash chromatography (SiO$_2$, Hexane/EtOAc (5-3:1) to afford 12c (70 mg, 21%) as a white solid. $^1$H NMR (300 MHz, DMSO-d$_6$) δ 11.70 (br s, 1H), 7.45 (s, 1H), 1.93 (t, J=10.6 Hz, 3H), 1.47 (s, 9H).

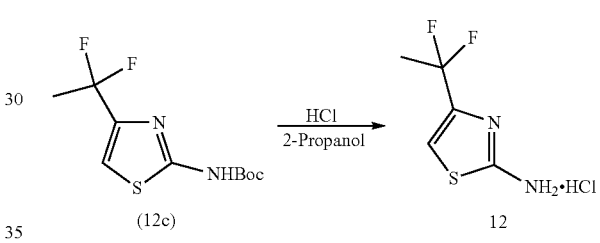

A solution of 12c (70 mg, 0.265 mmol) in 5M HCl in 2-Propanol (10 mL) was stirred at 0-24° C. for 7 hours. The volatiles were removed under reduced pressure to afford 12 as its hydrochloride salt (54 mg, 99%) as an off-white solid. $^1$H NMR (300 MHz, DMSO-d$_6$) δ 6.87 (s, 1H), 4.86 (br s, 3H), 1.88 (t, J=10.6 Hz, 3H). LCMS (ESI, m/z) 165.3 [M+H for free amine 12]+.

Example 3

Compound 30

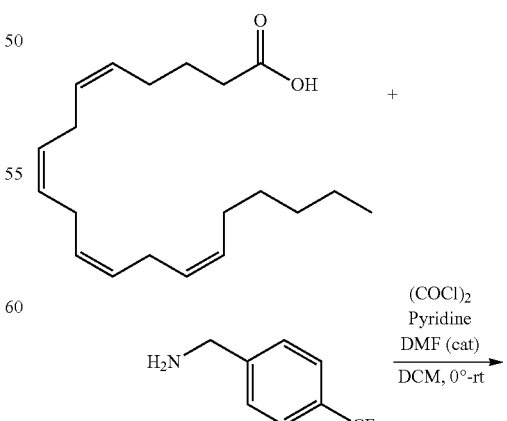

-continued

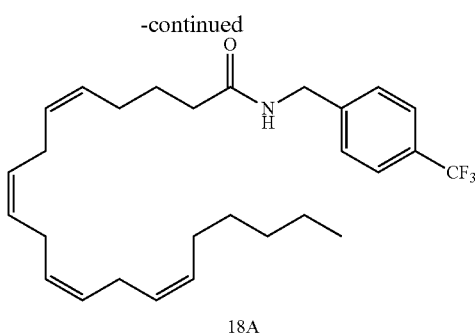

18A

A solution of (5Z,8Z,11Z,14Z)-icosa-5,8,11,14-tetraenoic acid (200 mg, 0.58 mmol) in DCM (4 ml) and DMF (0.12 ml) was cooled to 0° C. and oxalyl chloride (0.116 ml, 1.31 mmol) was added dropwise. The reaction mixture was stirred for an additional 1 h followed by the addition of a solution of 18 (200 mg, 1.15 mmol) in pyridine (0.493 ml, 0.493 mmol). The mixture was warmed to rt and stirred for an additional 30 minutes. The mixture was diluted with DCM (5 mL) and washed with 10% aq. HCl and water. The organic layer was dried ($Na_2SO_4$), concentrated and purified by flash SiO2 chromatography (Hexanes/EtOAc) to provide 18A (77 mg, 29% yield) as a pale yellow oil: $^1$H NMR (400 MHz, CDCl3) δ 7.56-7.58 (d, J=8.00 Hz, 2H), 7.37-7.39 (d, J=8.00 Hz, 2H), 5.81 (s, 1H), 5.33-5.40 (m, 8H), 4.48-4.49 (d, J=6.00 Hz, 2H), 2.79-2.82 (m, 6H), 2.22-2.56 (t, J=7.60 Hz, 2H), 2.12-2.13 (m, 2H), 2.03-2.05 (m, 2H), 1.73-1.77 (m, 2H), 1.27-1.35 (m, 6H), 0.88 (t, J=6.80 Hz, 3H); $C_{28}H_{38}F_3NO$ Exact Mass: 461.29 ESI$^+$ m/z 493.1 [M+Na]$^+$.

Example 4

Compound 31

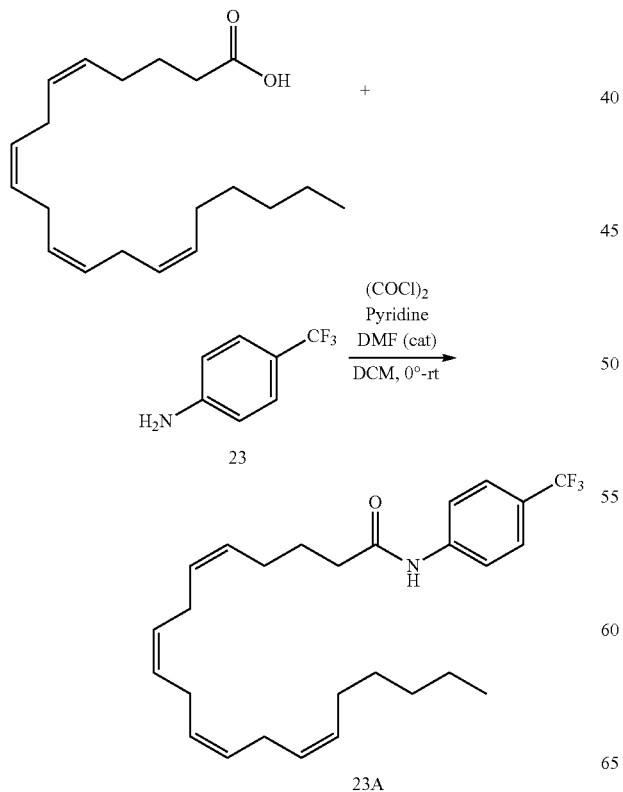

A solution of (5Z,8Z,11Z,14Z)-icosa-5,8,11,14-tetraenoic acid (200 mg, 0.58 mmol) in DCM (4 ml) and DMF (0.12 ml) was cooled to 0° C. and oxalyl chloride (0.116 ml, 1.31 mmol) was added dropwise. The reaction mixture was stirred for an additional 1 h followed by the addition of a solution of 23 (200 mg, 1.24 mmol) in pyridine (0.493 ml, 0.493 mmol). The mixture was warmed to rt and stirred for an additional 30 minutes. The mixture was diluted with DCM (5 mL) and washed with 10% aq. HCl and water. The organic layer was dried ($Na_2SO_4$), concentrated and purified by flash SiO2 chromatography (Hexanes/EtOAc) to provide 23A (70 mg, 27% yield) as a pale yellow oil: $^1$H NMR (400 MHz, CDCl3) δ 7.62-7.65 (d, J=8.80 Hz, 2H), 7.55-7.57 (d, J=8.8 Hz, 2H), 7.30 (s, 1H), 5.34-5.43 (m, 8H), 2.80-2.82 (m, 6H), 2.38-2.41 (t, J=7.60 Hz, 2H), 2.17-2.19 (m, 2H), 2.04-2.06 (m, 2H), 1.81-1.85 (m, 2H), 1.28-1.31 (m, 6H), 0.88 (t, J=6.80 Hz, 3H); $C_{27}H_{36}F_3NO$ Exact Mass: 447.27 ESI$^+$ m/z 470.1 [M+Na]$^+$.

Example 5

Compounds of Formula (I)

For some compounds, the foregoing syntheses are exemplary and can be used as a starting point to prepare additional compounds of Formula (I), while some compounds of Formula (I), or a salt thereof, can be obtained from a commercial source. Examples of additional compounds of Formula (I) are shown below. These compounds can be prepared in various ways, including those synthetic schemes shown and described herein. Those skilled in the art will be able to recognize modifications of the disclosed syntheses and to devise routes based on the disclosures herein; all such modifications and alternate.

| Structure | Compound No. |
|---|---|
| ![structure 1] | 1 |
| ![structure 2] | 2 |
| ![structure 3] | 3 |
| ![structure 4] | 4 |
| ![structure 5] | 5 |
| ![structure 6] | 6 |

-continued

| Structure | Compound No. |
|---|---|
| 4-tert-butyl-thiazol-2-yl-methanamine | 7 |
| 4-trifluoromethyl-thiazol-2-yl-methanamine | 8 |
| 2-(4-trifluoromethyl-thiazol-2-yl)-ethanamine | 9 |
| 4-tert-butyl-thiazol-2-amine | 10 |
| (2-methyl-thiazol-5-yl)-methanamine | 13 |
| (2-methyl-thiazol-4-yl)-methanamine | 14 |
| (1-ethyl-1H-pyrazol-4-yl)-methanamine | 15 |
| 4,5-dimethyl-oxazol-2-amine | 16 |
| (1,5-dimethyl-1H-pyrazol-3-yl)-methanamine | 17 |
| 2-tert-butyl-pyrimidin-4-amine | 19 |

-continued

| Structure | Compound No. |
|---|---|
| 4-trifluoromethyl-pyrimidin-2-amine | 20 |
| 6-trifluoromethyl-pyridin-2-amine | 21 |
| 5-trifluoromethyl-pyrimidin-2-amine | 22 |
| (6-trifluoromethyl-pyridin-2-yl)-methanamine | 24 |
| 2-(4-trifluoromethyl-phenyl)-ethanamine | 25 |
| N-(4-hydroxyphenyl)-pivalamide | 26 |
| N-(4-trifluoromethyl-benzyl)-acetamide | 27 |
| N-(4-tert-butyl-phenyl)-acetamide | 28 |

-continued

| Structure | Compound No. |
|---|---|
| 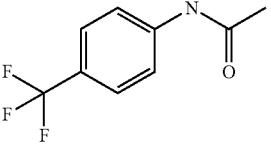 | 29 |
| 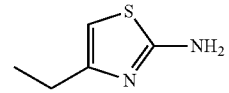 | 30 |
| 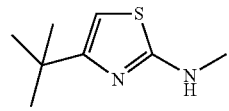 | 31 |
| 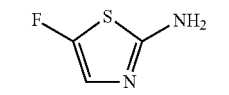 | 32 |
| 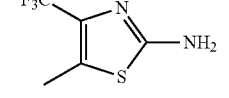 | 33 |
| 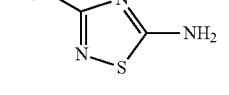 | 34 |
| 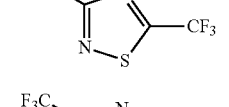 | 35 |
| 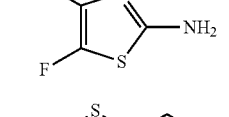 | 36 |
| 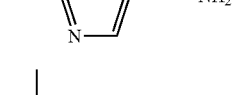 | 37 |
| 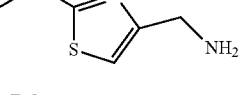 | 38 |
| 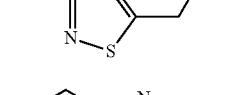 | 39 |
| 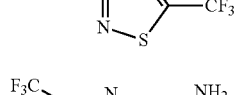 | 40 |
| 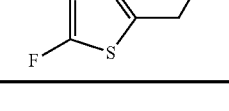 | 41 |

Example A

Formalin Paw Test

One test compound or the vehicle was administered to each mouse in each test group (8 mice per group). Non-fasted male ICR mice weighing 23±3 g were used. Test compounds were administered at a concentration of 30 mg/kg, 100 mg/kg or 200 mg/kg; morphine was administered at a concentration of 10 mg/kg; and acetaminophen was administered at a concentration of >100 mg/kg. The control group received the vehicle (5% DMSO/15% PEG400/10% HPbCD/0.9% Saline). After 10 minutes, a 2% formalin solution (0.02 mL) was injected into one hind paw (sub-plantar) of each mouse. Responses were measured every 5 minutes after the formalin injection for 35 minutes.

The results are provided in Tables A, B and C. As shown in Tables A, B, and C compounds of Formula (I) significantly decreased the pain response in both the early/acute phase (0-10 minutes) and the late/tonic phase (10-35 minutes). The results in Table A are for oral administration; the results in Table B are for intraperitoneal administration; the results in Table C are for intravenous administration. In Tables A, B, and C, 'A' designates <70 licks/sec, 'B' designates ≥70 licks/sec and <165 licks/sec, and 'C' designates ≥165 licks/sec.

TABLE A

| Compound No. | Dosage (mg/kg) | Early Phase | Late Phase |
|---|---|---|---|
| 26 | 200 | B | B |
| 28 | 200 | B | B |
| 29 | 200 | A | A |

TABLE B

| Compound No. | Dosage (mg/kg) | Early Phase | Late Phase |
|---|---|---|---|
| 1 | 30 | B | C |
| 2 | 30 | B | C |
| 3 | 30 | A | B |
| 4 | 30 | B | C |
| 5 | 30 | B | C |
| 6 | 30 | B | C |
| 7 | 30 | B | A |
| 8 | 30 | A | A |
| 9 | 30 | A | A |
| 10 | 30 | A | A |
| 11 | 30 | B | C |
| 12 | 30 | B | A |
| 13 | 30 | B | C |
| 14 | 30 | B | C |
| 15 | 30 | B | A |
| 16 | 30 | A | A |
| 17 | 30 | B | B |
| 18 | 30 | B | C |
| 19 | 30 | B | C |
| 20 | 30 | B | C |
| 21 | 30 | B | C |
| 22 | 30 | B | C |
| 23 | 30 | A | A |
| 24 | 30 | B | C |
| 25 | 30 | A | B |

TABLE C

| Compound No. | Dosage (mg/kg) | Early Phase | Late Phase |
|---|---|---|---|
| 27 | 100 | A | A |

Example B

Glutathione Conjugation Assay

An incubation mixture consisting of 5 μL of 10 mM test compound in DMSO (5 μL of DMSO for negative control; 5 μL of 10 mM acetaminophen in DMSO for positive control), 5 μL of 0.1 M glutathione 25 mM EDTA in water, 50 μL of 100 mM MgCl$_2$ in water, 50 μL of 20 mg/mL pooled human liver microsomes (P-450 content: ~0.5 nmol/mg protein), and 340 μL of 100 mM potassium phosphate buffer (pH 7.4) is preincubated at 37° C. for 10 mins. The reaction is initiated by the addition of 50 μL of 100 mM NADPH solution. The final incubation volume is 0.5 mL. The incubation mixture contains 100 μM test compound or acetaminophen (positive control), 1 mM glutathione, and 1 μM P450. After 60 mins incubation at 37° C., 1 mL of chilled acetonitrile is added to stop the reaction. After the addition of acetonitrile, the sample is vortexed and centrifuged. The supernatant is collected, concentrated in TurboVap under N$_2$ (10 psi) at 30° C. for 35 mins, and transferred to a 96-well plate. The plate is capped and centrifuged. The supernatant is injected for LC-MS/MS analysis.

As one of skill in the art will appreciate, acetaminophen can form the reactive metabolite N-acetyl-p-benzoquinone imine (NAPQI) in vivo, which is linked to liver toxicity. Not wishing to be limited by theory, it is thought that acetaminophen is metabolically activated by cytochrome P450 enzymes to form NAPQI, and NAPQI in turn depletes endogenous glutathione (GSH). The depletion of endogenous glutathione leaves cells vulnerable to oxidative damage. The formation of NAPQI is the result of the susceptibility to oxidation of the electron rich substituted phenyl ring of acetaminophen. Because the ring is substituted with an —OH and —NH groups para- to each other, in the absence of other moieties, acetaminophen can be oxidized to NAPQI.

Unlike acetaminophen, compounds of Formula (I) do not include phenyl substitution like that of acetaminophen. Unlike acetaminophen, compounds of Formula (I) do not include substitution like that of acetaminophen. In some embodiments, a compound of Formula (I) does not include a phenyl ring. In some embodiments, a compound of Formula (I), or otherwise provided herein, does not include a para-phenyl —OH—NH substitution. In some embodiments, a compound of Formula (I) includes other substituents on a phenyl ring that prevent or retard oxidation in the body to a quinone imine. In some embodiments, a compound of Formula (I) includes other substituents on a phenyl ring that prevent or retard reaction with glutathione. As a result, one skilled in the art would not expect compounds of Formula (I) as provided herein to form the reactive metabolite NAPQI, or any other reactive quinone imine metabolite. A 129 neutral loss scan can be used to search or detect the formation of glutathione conjugates of reactive metabolites.

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A method for reducing or at least partially preventing pain or fever comprising administering an effective amount of a medicament comprising any of the compound selected from the group consisting of:

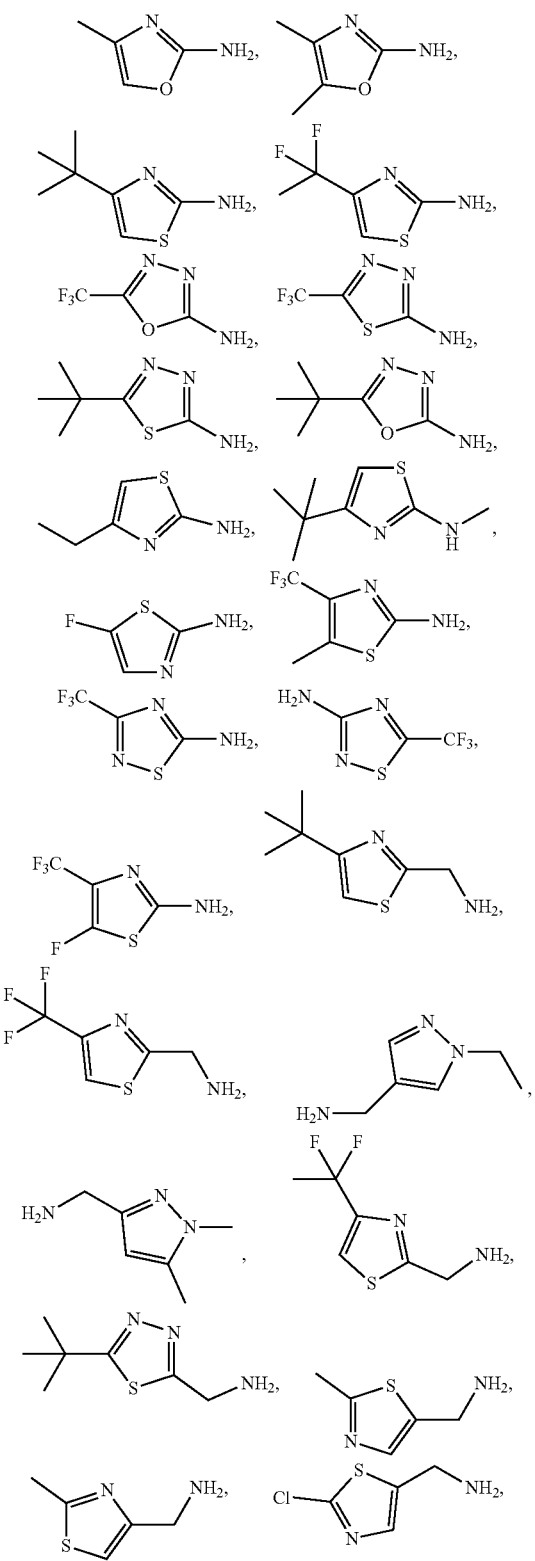

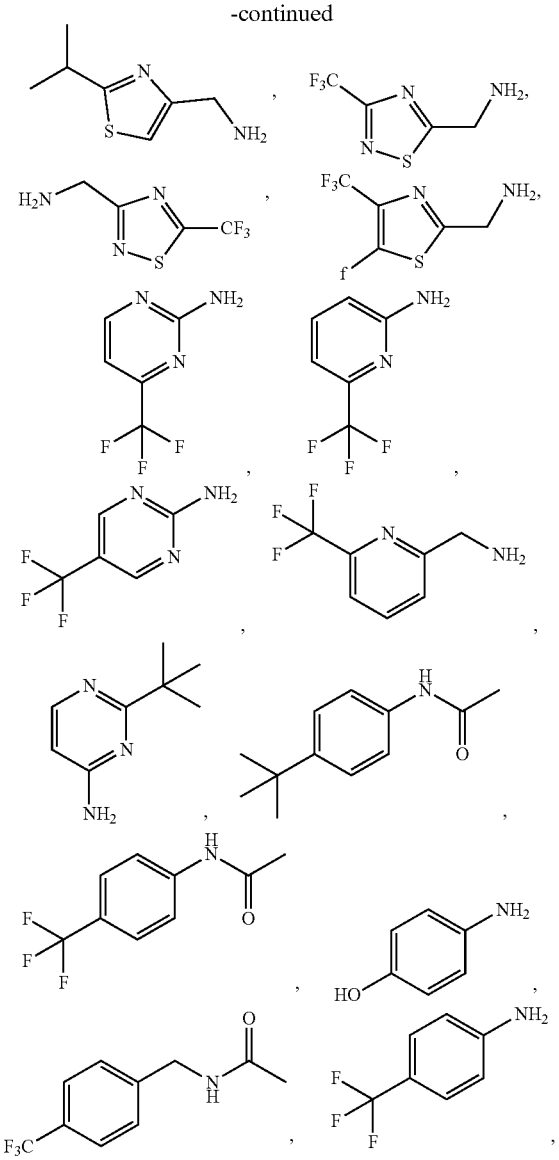

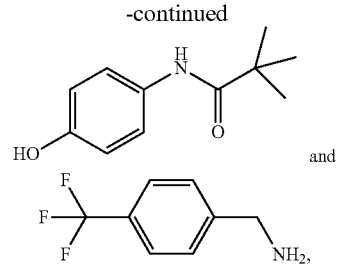

or a pharmaceutically acceptable salt of any of the foregoing.

2. The method of claim 1, further comprising administering an opioid analgesic in combination.

3. The method of claim 2, wherein the opioid analgesic is selected from the group consisting of morphine, codeine, hydrocodone, oxycodone, fentanyl, pethidine, methadone, pentazocine, sufentanil, levorphanol, dihydrocodeine, nalbuphine, butorphanol, tramadol, meptazinol, buprenorphine, dipipanone, alfentanil, remifentanil, oxymorphone, tapentadol, propoxyphene and hydromorphone.

4. The method of claim 1, wherein the compound is administered intravenously, administered orally or administered intraperitoneally.

5. The method of claim 1, wherein the pain is acute pain.

6. The method of claim 1, wherein the pain is post-operative pain.

7. The method of claim 1, wherein the pain is chronic pain.

8. The method of claim 1, wherein the pain is nociceptive pain.

9. The method of claim 1, wherein the pain is selected from the group consisting of osteoarthritis pain, rheumatoid arthritis pain, migraine pain, lower back pain, cancer pain and fibromyalgia pain.

10. The method of claim 1, wherein the pain is neuropathic pain.

11. The method of claim 1, wherein the pain is visceral pain.

12. The method of claim 1, wherein the pain is mixed pain.

* * * * *

UNITED STATES PATENT AND TRADEMARK OFFICE
CERTIFICATE OF CORRECTION

Page 1 of 2

PATENT NO. : 10,653,681 B2
APPLICATION NO. : 16/085505
DATED : May 19, 2020
INVENTOR(S) : Kevin Duane Bunker It is certified that error appears in the above-identified patent and that said Letters Patent is hereby corrected as shown below:

On the Title Page

Column 1, Item (72), Line 4, under Inventors, delete "diego" and insert --Diego--.

On Page 2, Column 1, Item (56), Line 2, under U.S. Patent Documents, delete "Norwell et al." and insert --Horwell et al.--.

On Page 2, Column 2, Item (56), Line 25, under Other Publications, delete "FMSlike" and insert --FMS like--.

On Page 2, Column 2, Item (56), Line 46, under Other Publications, delete "Fluoxentine of" and insert --Fluoxetine on--.

On Page 2, Column 2, Item (56), Line 51, under Other Publications, delete "12" and insert --I2--.

On Page 2, Column 2, Item (56), Line 69, under Other Publications, delete "and" and insert --und--.

In the Specification

In Column 12, Line 2, delete "L" and insert --$Z^{10}$--.

In Column 15, Line 11 (Approx.), delete "tut" and insert --tert--.

In Column 15, Line 22 (Approx.), delete "B" and insert --$B^1$--.

In Column 15, Line 36, delete "$C_{IA}$" and insert --$C_{1-8}$--.

In Column 19, Line 37, delete "(CH$_2$)$_7$CH=CH(CH$_2$)$_3$CH$_3$," and insert -- —(CH$_2$)$_7$CH=CH(CH$_2$)$_3$CH$_3$--.

Signed and Sealed this
Twenty-second Day of September, 2020

Andrei Iancu
*Director of the United States Patent and Trademark Office*

CERTIFICATE OF CORRECTION (continued)

In Column 20, Line 1, delete "linoleiaidic" and insert --linolelaidic--.

In Column 25, Line 12 (Approx.), delete "B" and insert --B$^1$--.

In Column 25, Line 41 (Approx.), delete "pyridizinyl" and insert --pyridazinyl--.

In Column 36, Line 67, delete "thereof" and insert --thereof;--.

In Column 39, Line 2, delete "EST$^+$" and insert --ESI$^+$--.

In Column 39, Line 46 (Approx.), delete "CDCL$_3$" and insert --CDCl$_3$--.

In Column 40, Line 24 (Approx.), delete "br s" and insert --brs--.

In Column 40, Line 40, delete "br s" and insert --brs--.

In Column 41, Line 26 (Approx.), delete "CDCl3" and insert --CDCl$_3$--.

In Column 42, Line 13, delete "CDCl3" and insert --CDCl$_3$--.

In the Claims

In Column 49, Lines 7-12 (Approx.), Claim 1, delete " 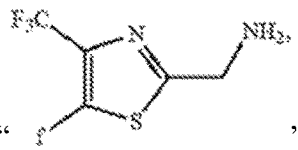 " and insert -- 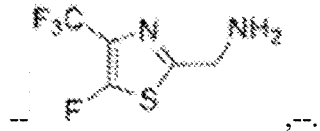 ,--.